(12) United States Patent
Mamet et al.

(10) Patent No.: US 9,700,624 B2
(45) Date of Patent: Jul. 11, 2017

(54) FORMULATIONS FOR THE DELIVERY OF ACTIVE INGREDIENTS

(71) Applicant: Adynxx, Inc., San Francisco, CA (US)

(72) Inventors: Julien Mamet, San Francisco, CA (US); Scott Harris, San Francisco, CA (US); George Miljanich, San Francisco, CA (US); Rick Orr, San Francisco, CA (US); William K Schmidt, San Francisco, CA (US); Tony Yaksh, San Francisco, CA (US); David C Yeomans, San Francisco, CA (US)

(73) Assignee: Adynxx, Inc., San Francisco, CA (US)

( * ) Notice: Subject to any disclaimer, the term of this patent is extended or adjusted under 35 U.S.C. 154(b) by 0 days.

(21) Appl. No.: 14/399,235

(22) PCT Filed: May 9, 2013

(86) PCT No.: PCT/US2013/040426
§ 371 (c)(1),
(2) Date: Nov. 6, 2014

(87) PCT Pub. No.: WO2013/170086
PCT Pub. Date: Nov. 14, 2013

(65) Prior Publication Data
US 2015/0111956 A1    Apr. 23, 2015

Related U.S. Application Data

(60) Provisional application No. 61/645,475, filed on May 10, 2012.

(51) Int. Cl.
| | | |
|---|---|---|
| C07H 21/04 | (2006.01) |
| A61K 47/02 | (2006.01) |
| A61K 45/06 | (2006.01) |
| A61K 31/713 | (2006.01) |
| A61K 9/00 | (2006.01) |
| A61K 38/00 | (2006.01) |

(52) U.S. Cl.
CPC .......... *A61K 47/02* (2013.01); *A61K 9/0019* (2013.01); *A61K 31/713* (2013.01); *A61K 45/06* (2013.01); *A61K 38/00* (2013.01)

(58) Field of Classification Search
CPC ...................................................... C07H 21/04
See application file for complete search history.

(56) References Cited

U.S. PATENT DOCUMENTS

| | | |
|---|---|---|
| 5,206,152 A | 4/1993 | Sukhatme |
| 5,504,075 A | 4/1996 | Burrows et al. |
| 5,683,985 A | 11/1997 | Chu et al. |
| 6,004,813 A | 12/1999 | Serlupi-Crescenzi et al. |
| 6,008,048 A | 12/1999 | Monia et al. |
| 6,011,143 A | 1/2000 | Shionoya et al. |
| 6,022,863 A | 2/2000 | Peyman |
| 6,034,234 A | 3/2000 | Matsuo |
| 6,060,310 A | 5/2000 | Cho-Chung |
| 6,140,128 A | 10/2000 | Cohen et al. |
| 6,262,033 B1 | 7/2001 | Morishita et al. |
| 6,270,761 B1 | 8/2001 | Russell et al. |
| 6,316,190 B1 | 11/2001 | Rein et al. |
| 6,333,408 B1 | 12/2001 | Motojima et al. |
| 6,395,029 B1 | 5/2002 | Levy |
| 6,410,516 B1 | 6/2002 | Baltimore et al. |
| 6,410,721 B1 | 6/2002 | Hunt et al. |
| 6,432,641 B1 | 8/2002 | Lee et al. |
| 6,555,525 B2 | 4/2003 | Burke |
| 6,599,741 B1 | 7/2003 | Hecker et al. |
| 6,774,118 B1 | 8/2004 | Dzau et al. |
| 6,818,626 B1 | 11/2004 | Wolff et al. |
| 6,821,956 B2 | 11/2004 | Dzau et al. |
| 6,867,289 B1 | 3/2005 | Gorenstein et al. |
| 6,890,909 B1 | 5/2005 | Ono et al. |
| 6,927,027 B2 | 8/2005 | Erikson et al. |
| 6,969,704 B1 | 11/2005 | Pinsky et al. |
| 7,014,861 B2 | 3/2006 | Roorda et al. |
| 7,060,690 B2 | 6/2006 | Klem |
| 7,108,844 B2 | 9/2006 | Carpentier |
| 7,160,869 B2 | 1/2007 | Lee et al. |
| 7,186,556 B2 | 3/2007 | Hecker et al. |
| 7,256,182 B2 | 8/2007 | Lawrence, III et al. |
| 7,320,964 B2 | 1/2008 | Hecker et al. |
| 7,482,158 B2 | 1/2009 | Mathison |
| 7,524,949 B2 | 4/2009 | Hecker et al. |
| 7,585,848 B2 | 9/2009 | Masuda et al. |

(Continued)

FOREIGN PATENT DOCUMENTS

| | | |
|---|---|---|
| CA | 2583576 | 4/2006 |
| EP | 0572287 A2 | 12/1993 |

(Continued)

OTHER PUBLICATIONS

Office Action, Japanese Application No. 201380036825.2, mailed Jan. 15, 2016, 5 pages.
Search Report, Japanese Application No. 201380036825.2, mailed Jan. 7, 2016, 5 pages.
Victor J. Dzau, "Transcription Factor Decoy," Circulation Research, 2002, vol. 90, pp. 1234-1236.
International Preliminary Report on Patentability for PCT Application No. PCT/US2013/040426 mailed Nov. 11, 2014 (7 pages).
Written Opinion for PCT Application No. PCT/US2013/040426 mailed Nov. 26, 2013 (6 pages).
International Search Report for PCT Application No. PCT/US2013/040426 mailed Nov. 26, 2013 (5 pages).
Altschul et al., "BLAST Manual", Natl. Cent. Biotechnol. Inf., Natl. Library Medicine.

(Continued)

*Primary Examiner* — Kimberly Chong
(74) *Attorney, Agent, or Firm* — Cooley LLP

(57) ABSTRACT

This invention relates generally to in vivo delivery of active ingredient formulations. More particularly, this invention relates to formulations of active ingredients that further comprise an agent, methods of making such formulations, and methods of using the same.

28 Claims, 5 Drawing Sheets

(56) References Cited

U.S. PATENT DOCUMENTS

| | | | |
|---|---|---|---|
| 7,777,014 | B2 | 8/2010 | Cattaruzza et al. |
| 7,943,591 | B2 | 5/2011 | Mamet |
| 8,093,225 | B2 | 1/2012 | Mamet |
| 8,741,864 | B2 | 6/2014 | Mamet |
| 8,808,747 | B2 | 8/2014 | Brown et al. |
| 9,290,762 | B2 | 3/2016 | Mamet |
| 2002/0192184 | A1 | 12/2002 | Carpentier |
| 2003/0166555 | A1 | 9/2003 | Alberini et al. |
| 2004/0048820 | A1 | 3/2004 | Hecker et al. |
| 2004/0192598 | A1 | 9/2004 | Kragie |
| 2004/0229833 | A1 | 11/2004 | Dzau et al. |
| 2005/0192238 | A1 | 9/2005 | Hecker et al. |
| 2006/0069055 | A1 | 3/2006 | Dajee et al. |
| 2006/0116344 | A1 | 6/2006 | Morishita et al. |
| 2006/0122134 | A1 | 6/2006 | Cattaruzza et al. |
| 2006/0153847 | A1 | 7/2006 | Masuda |
| 2006/0154886 | A1 | 7/2006 | Weihe et al. |
| 2006/0166916 | A1 | 7/2006 | Mathison |
| 2006/0189564 | A1 | 8/2006 | Burright et al. |
| 2006/0293264 | A1 | 12/2006 | Grandis et al. |
| 2012/0046348 | A1* | 2/2012 | Vaillant ............ A61K 31/7088 514/44 R |
| 2013/0309201 | A1 | 11/2013 | Bazinet et al. |
| 2014/0343132 | A1 | 11/2014 | Mamet |
| 2016/0222382 | A1 | 8/2016 | Mamet |

FOREIGN PATENT DOCUMENTS

| | | |
|---|---|---|
| EP | 1281763 A2 | 2/2003 |
| EP | 1298141 A1 | 4/2003 |
| EP | 1357184 A2 | 10/2003 |
| EP | 1690544 A2 | 8/2006 |
| JP | 2005-336081 A | 12/2005 |
| JP | 2010-526541 A | 9/2013 |
| JP | 2013-536195 A | 9/2013 |
| KR | 2005-0016361 A | 2/2005 |
| WO | WO 96/29433 A1 | 9/1996 |
| WO | WO 99/26634 A1 | 6/1999 |
| WO | WO 02/29044 A2 | 4/2002 |
| WO | WO 02/41922 A1 | 5/2002 |
| WO | WO 02/066071 A2 | 8/2002 |
| WO | WO 02/070668 A2 | 9/2002 |
| WO | WO 03/063799 A2 | 8/2003 |
| WO | WO 03/091432 A1 | 11/2003 |
| WO | 2004052401 A2 | 6/2004 |
| WO | 2005004702 A2 | 1/2005 |
| WO | WO 2005/027830 A2 | 3/2005 |
| WO | WO 2006/035434 A2 | 4/2006 |
| WO | WO 2006/043722 A1 | 4/2006 |
| WO | WO 2006/086105 A2 | 8/2006 |
| WO | WO 2006/096498 A2 | 9/2006 |
| WO | WO 2008/141308 A2 | 11/2008 |
| WO | WO 2012/021985 A1 | 2/2012 |
| WO | WO 2012/177906 A1 | 12/2012 |
| WO | WO 2016/025829 A1 | 2/2016 |

OTHER PUBLICATIONS

Altschul et al., "Gapped BLAST and PSI-BLAST: a new generation of protein database search programs", Nucelic Acid Research, 1997, pp. 3389-3402, vol. 25, No. 17.

Yisheng Xu et al., "Multime rization and Aggregation of Native-State Insulin: Effect of Zinc," Langmuir, Jan. 10, 2012, pp. 579-586, vol. 28, No. 1.

European Search Report, European Patent Application No. 13787024, mailed Dec. 8, 2015, 9 pages.

Ahn et al., "Inhibitory effects of novel AP-1 decoy oligodeoxynucleotides on vascular smooth muscle cell proliferation in vitro and neointimal formation in vivo", Circ Res, 90:1325-1332 (2002).

Australian Application No. 2008251320, Examination Report mailed Sep. 4, 2012, 4 pages.

Australian Application No. 2014201462, Examination Report mailed Sep. 4, 2015, 4 pages.

Australian Application No. 2014201462, Examination Report mailed Jun. 30, 2016, 3 pages.

Borner et al., STAT6 transcription factor binding sites with mismatches within the canonicai 5'-TTC . . . GAA-3' motif involved in regulation of delta- and mu-opioid receptors, J Neurochem, 91[6]:1493-1500 (2004).

Buchwald et al., "Decoy oligodeoxynucleotide against activator protein-1 reduces neointimal proliferation after coronary angioplasty in hypercholesterolemic minipigs", JACC, 39:732-738 (2002).

Cattaruzza et al., "Mechanosensitive transcription factors involved in endothelin B receptor expression", J Bioi Chem, 276[40]:36999-37003 (2001).

Chen et al., "Up-regulation of Egr1 by 1.25-dihydroxyvitamin D3 contributes to increased expression of p35 activator of cyclin-dependent kinase 5 and consequent onset of the terminal phase of HL60 cell differentiation", Cancer Res, 64[15]:5425-5433 (2004).

Cho et al., "A genomic-scale view of the cAMP response element-enhancer decoy: a tumor target based genetic tool", PNAS, 99[24]:15626-15631 (2002).

Cho et al., "Potentiation of lipopolysaccharide-inducible cyclooxygenase 2 expression by C2-ceramide via c-Jun N-terminal kinase-mediated activation of CCAAT/enhancer binding protein in macrophages", Mol Pharmacol, 63[3]:512-523 (2003).

D'Acquisto et al., "Local administration of transcription factor decoy oligonucleotides to nuclear factor-kB prevents carrageenin-induced inflammation in rat hind paw", Gene Ther, 7[20]:1731-1737 (2000).

Daftary, Gaurang S., et al. "A novel role of the Sp/KLF transcription factor KLF11 in arresting progression of endometriosis." PloS One (2013); 8.3: e60165.

Dash et al., "Sequestration of serum response factor in the hippocampus impairs long-term spatial memory", J Neuroch, 93:269-278 (2005).

Enomoto, Takashi, et al. "Transcriptional regulation of an insulin-sensitizing adipokine adipolin/CTRP12 in adipocytes by Krüppel-like factor 15." PloS One (2013); 8.12: e83183.

European Application No. 08755344.2, Extended European Search Report dated Oct. 12, 2011, 9 pages.

Foti et al., "A nucleoprotein complex containing Sp1, C/EBPbeta, and HMGI-Y controls human insulin receptor gene transcription", Mol Cell Biol, 23[8]:2720-2732 (2003).

Gao et al., "A single decoy oligodeoxynucleotides targeting multiple oncoproteins produces strong anticancer effects", Mol Pharmacal, 70[5]:1621-1629 (2006).

Grote et al., "Stech-inducible expession of the angogenic facor CCN1 in vasular smooth muscle cells is mediated by Egr-1", J Biol Chem., 279[53]:55675-555681 (2004).

Gupta and Kone, "USF-1 and USF-2 trans-repress IL-1beta-induced iNOS transcription in mesangial cells", Am J Physical Cell Physiol, 283:C1065-1072 (2002).

Hasan and MacDonald, "Sp/Kruppel-like transcription factors are essential for the expression of mitochondrial glycerol phosphate dehydrogenase promoter B," Gene, 296(1-2):221-234 (2002).

Herdegen and Leah, "Inducible and constitutive transcription factors in the mammalian nervous system: control of gene expression by Jun, Fos and Krox, and CREB/ATF proteins", Brain Res Brain Res Rev., 28[3]:370-490 (1998).

Igwe, O.J., "Modulation of peripheral inflammation in sensory ganglia by nuclear factor kB decoy oligodeoxynucleotide: involvement of SRC kinase pathway", Neurosci Lett., 381[1-2]:114-119 (2005).

Ishibashi et al., "Sp1 decoy transfected to carcinoma cells suppresses the expression of vascular endothelial growth factor, transforming growth factor b1, and tissue factor and also cell growth and invasion activities", Cancer Res., 60:6531-6536 (2000).

International Search Report and Written Opinion, International Application No. PCT/US2008/063471, mailed Jan. 14, 2009, 9 pages.

International Preliminary Report on Patentability, International Application No. PCT/US2008/063471, mailed Nov. 17, 2009, 6 pages.

(56) References Cited

OTHER PUBLICATIONS

International Search Report and Written Opinion, International Application No. PCT/US2015/045268, mailed Oct. 28, 2015, 16 pages.

Japanese Application No. 2010-507728, Office Action mailed Feb. 1, 2013 (English translation), 10 pages.

Kamimura et al., "Platelet-derived growth factor induces tissue factor expression in vascular smooth muscle cells via activation of Egr-1", Hypertension, 44[6]:944-951 (2004).

Kelkenberg et al., "CCAAT/enhancer-binding protein decoy oligodeoxynucleotide inhibition of macrophage-rich vascular lesion formation in hypercholesterolemic rabbits", Arterioscler Thromb Vase Bioi., 22:949-954 (2004).

Ko, S.W. et al., "Selective Contribution of Egr1 (Zif/268) to Persistent Inflammatory Pain", Journal of Pain, 6[1]:12-20 (2005).

Kohlstedt, K. et al., "Signaling via the angiotensin-converting enzyme enhances the expression of cyclooxygenase-2 in endothelial cells", Hypertension, 45:126-132 (2005).

Kraus et al., "The role of nuclear factor kappaB in tumor necrosis factor-regulated transcription of the human mu-opioid receptor gene", Mol Pharmacol, 64[4]:876-884 (2003).

Lee et al., "Spinal NFKB activation induces COX2 upregulation and contributes to inflammatory pain hypersensitivity", Eur J Neurosci, 19:3375-3381 (2004).

Lei, Lei, et al. "The zinc finger transcription factor Klf7 is required for TrkA gene expression and development of nociceptive sensory neurons." Genes & development 19.11 (2005): 1354-1364.

Leong et al., "Targeted inhibition of Stat3 with a decoy oligonucleotide abrogates head and neck cancer cell growth", PNAS, 100[7]:4138-4143 (2003).

Lesniak and Kuznicki, "Binding and functional characteristics of two E-box motifs within the S1OOA6 (calcyclin) gene promoter", J Cell Biochem, 97[5]:1017-1024 (2006).

Lim et al., "Sequence-independent inhibition of RNA transcription by DNA dumbbells and other decoys", Nucl Acids Res., 25[3]:575-581 (1997).

Ma et al., "Intrathecal injection of cAMP response element binding protein (CREB) antisense oligonucloetide attenuates tactile allodynia caused by partial sciatic nerve ligation", Brain Research, 988:97-104 (2003).

Mann et al., "Ex-vivo gene therapy of human vascular bypass grafts with E2F decoy: the PREVENT single-centre randomised controlled trial", The Lancet, 354:1493-1498 (1999).

Morishita et al., "A gene therapy strategy using a transcription factor decoy of the E2F binding site inhibits smooth muscle proliferation in vivo", PNAS, 92:5855-5859 (1995).

Motojima et al., "Sp1-like activity mediates angotensin-II-induced plasminogen-activator inhibitor type-1 (PAI-1) gene expression in mesangial cells", Biochem J., 349:435-441 (2000).

Ohtani et al., "Inhibition of neointimal hyperplasia after balloon injury by cis-element 'decoy' of early growth response gene-1 in hypercholesterolemic rabbits", Gene Ther, 11[2]:126-132 (2004).

Park et al., "Dual blockade of cyclic AMP response element—(CRE) and AP-1-directed transcription by CRE-transcription factor decoy oligonucleotide gene-specific inhibition of tumor growth", J Biol Chem., 274[3]:1573-1580 (1999).

Rygh et al., "Local and descending circuits regulate long-term potentiation and zif268 expression in spinal neurons", Eur J Neuroscience, 24[3]:761-772 (2006).

Sahin et al., "Inactivation of Ets 1 transcription factor by a specific decoy strategy reduces rat C6 glioma cell proliferation and mmp-9 expression", Int J Mol Med, 15:771-776 (2005).

Sakaue, G. et al, "NF-kB decoy suppresses cytokine expression and thermal hyperalgesia in a rat neuropathic pain model", NeuroReport, 12[10]:2079-2084 (2001).

Sassa, Y. et al., "Functional role of Egr-1 mediating VEGF-induced tissue factor expression in the retinal capillary endothelium", Graefes Arch Clin Exp Ophthalmol, 240[12]:1003-1010 (2002).

Steiger et al., "cAMP response element-binding protein, activating transcription factor-4, and upstream stimulatory factor differentially control hippocampal $GABA_BR1a$ and $GABA_BR1b$ subunit gene expression through alternative promoters", J Neurosci, 24[27]:6115-6126 (2004).

Sun, T. et al., "Alleviation of neuropathic pain by intrathecal injection of antisense oligonucleotides to p65 subunit of NF-kappa B", British Journal of Anaesthesia, 97(4):553-558 (2006).

Suzuki et al., "Initial clinical cases of the use of a NF-kB decoy at the site of coronary stenting for the prevention of restenosis", Circ Journal, 68:270-271 (2004).

Swirnoff and Milbrandt, "DNA-Binding Specificity of NGFI-A and Related Zinc Finger Transcription Factors", Molecular and Cellular Biology, 15[4]:2275-2287 (1995).

Taimor et al., "Transcription activator protein 1 (AP-1) mediates alpha- but not beta-adrenergic hypertrophic growth responses in adult cardiomyocytes", Am J Physiol Heart Circ Physiol, 286[6]:H2369-H2375 (2004).

Tanaka et al., "Sequence-specific interaction of alpha-beta-anomeric double stranded DNA with the p50 subunit of NFKB: application to the decoy approach", Nucl Acids Res, 22[15]:3069-3074 (1994).

Uchida et al., "Ceramide reduction and transcriptional up-regulation of glucosylceramide synthase through doxorubicin-activated Sp1 in drug-resistant HL-60/ADR cells", Cancer Res, 64:6271-6279 (2004).

Verrecchia et al., "Blocking Sp1 transcription factor broadly inhibits extracellular matrix gene expression in vitro and in vivo: implications for the treatment of tissue fibrosis", J Invest Dermatol, 116[5]:755-763 (2001).

Viedt et al., "The terminal complement complex C5b-9 stimulates interleukin-6 production in human smooth muscle cells through activation of transcription factors NF-kB and AP-1", FASEB J, 14:2370-2372 (2000).

Wagner et al., "Decoy Oligodeoxoynucleotide characterization of transcription factors controlling endothelin-B receptor expression in vascular smooth muscle cells", Mol Pharmacol, 58[6]:1333-1340 (2000).

Wang et al., "Dose-related antiallodynic effects of cyclic AMP response element-binding protein-antisense oligonucleotide in the spared nerve injury model of neuropathic pain", Neuroscience,139[3]:1083-1093 (2006).

Xiang et al., "Egr-1 mediates SiO(2-driven transcription of membrane type I matrix metalloproteinase in macrophages", J Huazhong Univ Sci Technolog Med Sci, 27[1]:13-16 (2007).

Yang et al., "Thrombospondin-1 mediates distal tubule hypertrophy induced by glycated albumin", Biochem J, 379:89-97 (2004).

Zanetti et al., "Inhibition of Sp1 activity by a decoy PNA-DNA chimera prevents urokinase receptor expression and migration of breast cancer cells", Biochem Pharmacol., 70[9]:1277-1287 (2005).

Zhang, P. et al., "Egr-1 mediates hypoxia-inducible transcription of the NORG1 gene through an overlapping Egr-1/Sp1 binding site in the promoter", Cancer Research, 67(19):9125-9133 (2007).

Matsumoto, Nobukyuki, et al. "Cloning the cDNA for a new human zinc finger protein defines a group of closely related Krüppel-like transcription factors." Journal of Biological Chemistry (1998); 273.43: 28229-28237.

Shields, Janiel M., and Yang, Vincent W. "Identification of the DNA sequence that interacts with the gut-enriched Krüppel-like factor." Nucleic Acids Research (1998); 26.3: 796-802.

Dobi, A., and Agoston, D. V. "Submillimolar levels of calcium regulates DNA structure at the dinucleotide repeat (TG/AC) n." Proceedings of the National Academy of Sciences (1998); 95.11: 5981-5986.

Examination Report in European Patent Application No. 13787024.2, mailed dated Apr. 13, 2017, 8 pages.

\* cited by examiner

FIGURE 1A, 1B, and 1C

```
                        SEQUENCE LISTING

<160> NUMBER OF SEQ ID NOS: 53

<210> SEQ ID NO 1
<211> LENGTH: 31
<212> TYPE: DNA
<213> ORGANISM: Artificial Sequence
<220> FEATURE:
<223> OTHER INFORMATION: Transcription factor oligonucleotide decoy

<400> SEQUENCE: 1
ggcttatgca aattcgaatg caaatttgtc g                                    31

<210> SEQ ID NO 2
<211> LENGTH: 36
<212> TYPE: DNA
<213> ORGANISM: Artificial Sequence
<220> FEATURE:
<223> OTHER INFORMATION: Transcription factor oligonucleotide decoy

<400> SEQUENCE: 2
ctaagcccac gtgaccattg gccaggtgac cagatc                              36

<210> SEQ ID NO 3
<211> LENGTH: 34
<212> TYPE: DNA
<213> ORGANISM: Artificial Sequence
<220> FEATURE:
<223> OTHER INFORMATION: Transcription factor oligonucleotide decoy

<400> SEQUENCE: 3
gttatgcgtg ggcgataatg cgggggcgtt atag                                34

<210> SEQ ID NO 4
<211> LENGTH: 29
<212> TYPE: DNA
```

```
<213> ORGANISM: Artificial Sequence
<220> FEATURE:
<223> OTHER INFORMATION: Transcription factor oligonucleotide decoy

<400> SEQUENCE: 4
gcctccctga gctcattgac gtatctcgg                                    29

<210> SEQ ID NO 5
<211> LENGTH: 30
<212> TYPE: DNA
<213> ORGANISM: Artificial Sequence
<220> FEATURE:
<223> OTHER INFORMATION: Transcription factor oligonucleotide decoy

<400> SEQUENCE: 5
cgaatatgac tgagaatgac tcagatttgc                                   30

<210> SEQ ID NO 6
<211> LENGTH: 37
<212> TYPE: DNA
<213> ORGANISM: Artificial Sequence
<220> FEATURE:
<223> OTHER INFORMATION: Transcription factor oligonucleotide decoy

<400> SEQUENCE: 6
ggttctatga ttttggaatc ggattgtgca aagaagc                           37

<210> SEQ ID NO 7
<211> LENGTH: 34
<212> TYPE: DNA
<213> ORGANISM: Artificial Sequence
<220> FEATURE:
<223> OTHER INFORMATION: Transcription factor oligonucleotide decoy

<400> SEQUENCE: 7
gcttcaggat gtccatatta ggagatcttg ttcg                              34

<210> SEQ ID NO 8
<211> LENGTH: 34
<212> TYPE: DNA
<213> ORGANISM: Artificial Sequence
<220> FEATURE:
<223> OTHER INFORMATION: Transcription factor oligonucleotide decoy

<400> SEQUENCE: 8
ggccacagga tgtaggatgt ccatattagg atgc                              34

<210> SEQ ID NO 9
<211> LENGTH: 35
<212> TYPE: DNA
<213> ORGANISM: Artificial Sequence
<220> FEATURE:
<223> OTHER INFORMATION: Transcription factor oligonucleotide decoy

<400> SEQUENCE: 9
gttctctaaa aataaaaggc taaaaataaa agtcg                             35

<210> SEQ ID NO 10
<211> LENGTH: 30
<212> TYPE: DNA
<213> ORGANISM: Artificial Sequence
<220> FEATURE:
<223> OTHER INFORMATION: Transcription factor oligonucleotide decoy

<400> SEQUENCE: 10
attaggggcg gggtccgggg cggggtatta                                   30
```

<210> SEQ ID NO 11
<211> LENGTH: 35
<212> TYPE: DNA
<213> ORGANISM: Artificial Sequence
<220> FEATURE:
<223> OTHER INFORMATION: Transcription factor oligonucleotide decoy

<400> SEQUENCE: 11
gttatggcgg ggcggggcgg ggccgggcgg tttac                          35

<210> SEQ ID NO 12
<211> LENGTH: 29
<212> TYPE: DNA
<213> ORGANISM: Artificial Sequence
<220> FEATURE:
<223> OTHER INFORMATION: Transcription factor oligonucleotide decoy

<400> SEQUENCE: 12
ggcaatgtgg ttttagtgtg gttttacgg                                 29

<210> SEQ ID NO 13
<211> LENGTH: 36
<212> TYPE: DNA
<213> ORGANISM: Artificial Sequence
<220> FEATURE:
<223> OTHER INFORMATION: Transcription factor oligonucleotide decoy

<400> SEQUENCE: 13
gccgtttggg gtcatagaac cacaggaacc acacgg                         36

<210> SEQ ID NO 14
<211> LENGTH: 32
<212> TYPE: DNA
<213> ORGANISM: Artificial Sequence
<220> FEATURE:
<223> OTHER INFORMATION: Transcription factor oligonucleotide decoy

<400> SEQUENCE: 14
cattgcccgg aaatggaccg gatgtaattt cc                             32

<210> SEQ ID NO 15
<211> LENGTH: 40
<212> TYPE: DNA
<213> ORGANISM: Artificial Sequence
<220> FEATURE:
<223> OTHER INFORMATION: Transcription factor oligonucleotide decoy

<400> SEQUENCE: 15
gttcttggaa aataaatgga aaatagtgga aaataagtcg                     40

<210> SEQ ID NO 16
<211> LENGTH: 33
<212> TYPE: DNA
<213> ORGANISM: Artificial Sequence
<220> FEATURE:
<223> OTHER INFORMATION: Transcription factor oligonucleotide decoy

<400> SEQUENCE: 16
cgttcccact tcctgcgacc acttcctgcc ggg                            33

<210> SEQ ID NO 17
<211> LENGTH: 33
<212> TYPE: DNA
<213> ORGANISM: Artificial Sequence
<220> FEATURE:

```
<223> OTHER INFORMATION: Transcription factor oligonucleotide decoy

<400> SEQUENCE: 17
ctgcacctat aaatggccta taaatgggga tgc                                33

<210> SEQ ID NO 18
<211> LENGTH: 33
<212> TYPE: DNA
<213> ORGANISM: Artificial Sequence
<220> FEATURE:
<223> OTHER INFORMATION: Transcription factor oligonucleotide decoy

<400> SEQUENCE: 18
gcttatttcg cggaaggttt cccggaagtg gcg                                33

<210> SEQ ID NO 19
<211> LENGTH: 31
<212> TYPE: DNA
<213> ORGANISM: Artificial Sequence
<220> FEATURE:
<223> OTHER INFORMATION: Transcription factor oligonucleotide decoy

<400> SEQUENCE: 19
gctgtgcctt atctctttgg gataactggc g                                  31

<210> SEQ ID NO 20
<211> LENGTH: 32
<212> TYPE: DNA
<213> ORGANISM: Artificial Sequence
<220> FEATURE:
<223> OTHER INFORMATION: Transcription factor oligonucleotide decoy

<400> SEQUENCE: 20
gcttaatgaa taagaggaaa aatgcatgct gg                                 32

<210> SEQ ID NO 21
<211> LENGTH: 33
<212> TYPE: DNA
<213> ORGANISM: Artificial Sequence
<220> FEATURE:
<223> OTHER INFORMATION: Transcription factor oligonucleotide decoy

<400> SEQUENCE: 21
gttctgagat tgcacgatga gatttcacag tcg                                33

<210> SEQ ID NO 22
<211> LENGTH: 32
<212> TYPE: DNA
<213> ORGANISM: Artificial Sequence
<220> FEATURE:
<223> OTHER INFORMATION: Transcription factor oligonucleotide decoy

<400> SEQUENCE: 22
gtcccgcata aataatggca tccttaatcg cg                                 32

<210> SEQ ID NO 23
<211> LENGTH: 36
<212> TYPE: DNA
<213> ORGANISM: Artificial Sequence
<220> FEATURE:
<223> OTHER INFORMATION: Transcription factor oligonucleotide decoy

<400> SEQUENCE: 23
gtgcaggcaa gagtagagac aggcaagagt agatgc                             36
```

```
<210> SEQ ID NO 24
<211> LENGTH: 25
<212> TYPE: DNA
<213> ORGANISM: Artificial Sequence
<220> FEATURE:
<223> OTHER INFORMATION: Transcription factor oligonucleotide decoy

<400> SEQUENCE: 24
ccgccaataa ttaattatta aggcc                                        25

<210> SEQ ID NO 25
<211> LENGTH: 35
<212> TYPE: DNA
<213> ORGANISM: Artificial Sequence
<220> FEATURE:
<223> OTHER INFORMATION: Transcription factor oligonucleotide decoy

<400> SEQUENCE: 25
gcttcgttcc atttccggtc tcggtttccc cattc                             35

<210> SEQ ID NO 26
<211> LENGTH: 34
<212> TYPE: DNA
<213> ORGANISM: Artificial Sequence
<220> FEATURE:
<223> OTHER INFORMATION: Transcription factor oligonucleotide decoy

<400> SEQUENCE: 26
gctgctgtgg aatatcgacc tgtggaatat cgtg                              34

<210> SEQ ID NO 27
<211> LENGTH: 37
<212> TYPE: DNA
<213> ORGANISM: Artificial Sequence
<220> FEATURE:
<223> OTHER INFORMATION: Transcription factor oligonucleotide decoy

<400> SEQUENCE: 27
gccgtataaa tgtgctataa agtttttaag accgtgc                           37

<210> SEQ ID NO 28
<211> LENGTH: 29
<212> TYPE: DNA
<213> ORGANISM: Artificial Sequence
<220> FEATURE:
<223> OTHER INFORMATION: Transcription factor oligonucleotide decoy

<400> SEQUENCE: 28
gccgtataaa tgtgctataa aagccgtgc                                    29

<210> SEQ ID NO 29
<211> LENGTH: 26
<212> TYPE: DNA
<213> ORGANISM: Artificial Sequence
<220> FEATURE:
<223> OTHER INFORMATION: Transcription factor oligonucleotide decoy

<400> SEQUENCE: 29
atgctgcgct tttctccaat ctgcgg                                       26

<210> SEQ ID NO 30
<211> LENGTH: 40
<212> TYPE: DNA
<213> ORGANISM: Artificial Sequence
<220> FEATURE:
<223> OTHER INFORMATION: Transcription factor oligonucleotide decoy
```

<400> SEQUENCE: 30
cgttctccga ttggtcacgg actctccgat tggtcacggc         40

<210> SEQ ID NO 31
<211> LENGTH: 28
<212> TYPE: DNA
<213> ORGANISM: Artificial Sequence
<220> FEATURE:
<223> OTHER INFORMATION: Transcription factor oligonucleotide decoy

<400> SEQUENCE: 31
gcgcacccca gcctggctca cccacgcg                       28

<210> SEQ ID NO 32
<211> LENGTH: 37
<212> TYPE: DNA
<213> ORGANISM: Artificial Sequence
<220> FEATURE:
<223> OTHER INFORMATION: Transcription factor oligonucleotide decoy

<400> SEQUENCE: 32
gatcctttgc ctccttcgat cctttgcctc cttcaag             37

<210> SEQ ID NO 33
<211> LENGTH: 29
<212> TYPE: DNA
<213> ORGANISM: Artificial Sequence
<220> FEATURE:
<223> OTHER INFORMATION: Transcription factor oligonucleotide decoy

<400> SEQUENCE: 33
ggtgtttggg agagctttgg gaggatacg                      29

<210> SEQ ID NO 34
<211> LENGTH: 36
<212> TYPE: DNA
<213> ORGANISM: Artificial Sequence
<220> FEATURE:
<223> OTHER INFORMATION: Transcription factor oligonucleotide decoy

<400> SEQUENCE: 34
gctaatcact cagcatttcg gtgagggaag tgaaag              36

<210> SEQ ID NO 35
<211> LENGTH: 51
<212> TYPE: DNA
<213> ORGANISM: Artificial Sequence
<220> FEATURE:
<223> OTHER INFORMATION: Transcription factor oligonucleotide decoy

<400> SEQUENCE: 35
cctttcagca ccacggacag cgccagcttc agcaccacgg acagcgcctc g    51

<210> SEQ ID NO 36
<211> LENGTH: 36
<212> TYPE: DNA
<213> ORGANISM: Artificial Sequence
<220> FEATURE:
<223> OTHER INFORMATION: Transcription factor oligonucleotide decoy

<400> SEQUENCE: 36
ggatcgaaca tggagtcagt gagaaatcag gatcgg              36

<210> SEQ ID NO 37
<211> LENGTH: 35

```
<212> TYPE: DNA
<213> ORGANISM: Artificial Sequence
<220> FEATURE:
<223> OTHER INFORMATION: Transcription factor oligonucleotide decoy

<400> SEQUENCE: 37
ggatcgaagc cggagtcaag gaggcccctg atcgg                               35

<210> SEQ ID NO 38
<211> LENGTH: 39
<212> TYPE: DNA
<213> ORGANISM: Artificial Sequence
<220> FEATURE:
<223> OTHER INFORMATION: Transcription factor oligonucleotide decoy

<400> SEQUENCE: 38
ccgaaaggac aaaggtcaag tcgaaaggac aaaggtcag                           39

<210> SEQ ID NO 39
<211> LENGTH: 35
<212> TYPE: DNA
<213> ORGANISM: Artificial Sequence
<220> FEATURE:
<223> OTHER INFORMATION: Transcription factor oligonucleotide decoy

<400> SEQUENCE: 39
cgggagaaaa ttcgggaacg ttcaagaatt gtcgg                               35

<210> SEQ ID NO 40
<211> LENGTH: 34
<212> TYPE: DNA
<213> ORGANISM: Artificial Sequence
<220> FEATURE:
<223> OTHER INFORMATION: Transcription factor oligonucleotide decoy

<400> SEQUENCE: 40
gttatgcgtg ggcgtagatg cggggggcgtt atag                               34

<210> SEQ ID NO 41
<211> LENGTH: 16
<212> TYPE: DNA
<213> ORGANISM: Artificial Sequence
<220> FEATURE:
<223> OTHER INFORMATION: Transcription factor oligonucleotide decoy

<400> SEQUENCE: 41
gatgcgtggg cgtagg                                                    16

<210> SEQ ID NO 42
<211> LENGTH: 23
<212> TYPE: DNA
<213> ORGANISM: Artificial Sequence
<220> FEATURE:
<223> OTHER INFORMATION: Transcription factor oligonucleotide decoy

<400> SEQUENCE: 42
gtatgcgtgg gcggtgggcg tag                                            23

<210> SEQ ID NO 43
<211> LENGTH: 30
<212> TYPE: DNA
<213> ORGANISM: Artificial Sequence
<220> FEATURE:
<223> OTHER INFORMATION: Transcription factor oligonucleotide decoy

<400> SEQUENCE: 43
```

```
gttatgcgtt tgtagatgct ttcgttatag                                        30

<210> SEQ ID NO 44
<211> LENGTH: 20
<212> TYPE: DNA
<213> ORGANISM: Artificial Sequence
<220> FEATURE:
<223> OTHER INFORMATION: Transcription factor oligonucleotide decoy

<400> SEQUENCE: 44
gttatgcgtg ggcgatatag                                                   20

<210> SEQ ID NO 45
<211> LENGTH: 28
<212> TYPE: DNA
<213> ORGANISM: Artificial Sequence
<220> FEATURE:
<223> OTHER INFORMATION: Transcription factor oligonucleotide decoy

<400> SEQUENCE: 45
gatgcgtggg cgttgacgtg gaaaatgc                                          28

<210> SEQ ID NO 46
<211> LENGTH: 30
<212> TYPE: DNA
<213> ORGANISM: Artificial Sequence
<220> FEATURE:
<223> OTHER INFORMATION: Transcription factor oligonucleotide decoy

<400> SEQUENCE: 46
ctatttcgaa acgatctaca ttggcataac                                        30

<210> SEQ ID NO 47
<211> LENGTH: 22
<212> TYPE: DNA
<213> ORGANISM: Artificial Sequence
<220> FEATURE:
<223> OTHER INFORMATION: Transcription factor oligonucleotide decoy

<400> SEQUENCE: 47
cgttcccact tcctgcgacc gg                                                22

<210> SEQ ID NO 48
<211> LENGTH: 26
<212> TYPE: DNA
<213> ORGANISM: Artificial Sequence
<220> FEATURE:
<223> OTHER INFORMATION: Transcription factor oligonucleotide decoy

<400> SEQUENCE: 48
gggtgaaggc aagagtagag cggcgg                                            26

<210> SEQ ID NO 49
<211> LENGTH: 21
<212> TYPE: DNA
<213> ORGANISM: Artificial Sequence
<220> FEATURE:
<223> OTHER INFORMATION: Transcription factor oligonucleotide decoy

<400> SEQUENCE: 49
cgttctccga ttggtcacgc g                                                 21

<210> SEQ ID NO 50
<211> LENGTH: 26
<212> TYPE: DNA
<213> ORGANISM: Artificial Sequence
```

-continued

```
<220> FEATURE:
<223> OTHER INFORMATION: Transcription factor oligonucleotide decoy

<400> SEQUENCE: 50
gtactccctt tgcctccttc aaccgg                                           26

<210> SEQ ID NO 51
<211> LENGTH: 31
<212> TYPE: DNA
<213> ORGANISM: Artificial Sequence
<220> FEATURE:
<223> OTHER INFORMATION: Transcription factor oligonucleotide decoy

<400> SEQUENCE: 51
ccttattcag caccacggac agcgccattc g                                     31

<210> SEQ ID NO 52
<211> LENGTH: 23
<212> TYPE: DNA
<213> ORGANISM: Artificial Sequence
<220> FEATURE:
<223> OTHER INFORMATION: Transcription factor oligonucleotide decoy

<400> SEQUENCE: 52
gcgaaaggac aaaggtcagg cgg                                              23

<210> SEQ ID NO 53
<211> LENGTH: 25
<212> TYPE: DNA
<213> ORGANISM: Artificial Sequence
<220> FEATURE:
<223> OTHER INFORMATION: Transcription factor oligonucleotide decoy

<400> SEQUENCE: 53
ggcttgctgt ggaatatcga tggtg                                            25
```

FORMULATIONS FOR THE DELIVERY OF ACTIVE INGREDIENTS

CROSS-REFERENCE TO RELATED APPLICATION

This application is a national stage application, filed pursuant to 35 U.S.C §371, of International Application No. PCT/US2013/040426, filed on May 9, 2013, which claims the benefit of priority to U.S. Provisional Application No. 61/645,475, filed on May 10, 2012, the contents of which are hereby incorporated by reference in their entireties for all purposes.

FIELD OF THE INVENTION

This invention relates generally to in vivo delivery of active ingredient formulations. More particularly, this invention relates to formulations of active ingredients that further comprise an in vivo stabilizing amount of an agent, methods of making such formulations, and methods of using the same.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ADDY_002_01US_ST25.txt, date recorded: Nov. 5, 2014, file size 11.4 kilobytes).

BACKGROUND OF THE INVENTION

Active ingredients, such as drugs that contain peptides, proteins, nucleic acids, or small organic molecules, may cause unwanted effects upon in vivo administration, such as to a mammal (e.g., a human). Such effects can detract significantly from the therapeutic benefit offered by the active ingredient itself. Accordingly, a need exists for formulations of active ingredients that minimize unwanted effects of in vivo administration.

SUMMARY OF THE INVENTION

The present invention is based, in part, on the discovery that homeostatic levels of certain agents are important with respect to adverse effect(s) of a therapeutic entity, e.g., an active ingredient of a therapeutic entity. Accordingly the present invention provides compositions or formulations capable of inhibiting or reducing adverse effect(s) of a therapeutic entity. In addition, the present invention also provides methods of using the composition or formulations for therapeutic treatments.

In one embodiment, the present invention provides a composition, such as a pharmaceutical composition, comprising an active ingredient and an in vivo stabilizing amount of an agent, wherein the agent is associated with an adverse effect in vivo caused by the administration of the active ingredient without the agent, and wherein the in vivo stabilizing amount is the amount that substantially saturates the binding sites of the active ingredient to the agent.

In another embodiment, the present invention provides a method of reducing an adverse effect of an active ingredient comprising administering the active ingredient with an in vivo stabilizing amount of an agent, wherein the agent is associated with the adverse effect of the active ingredient caused by the administration of the active ingredient without the agent, and wherein the in vivo stabilizing amount is the amount that substantially saturates the binding sites of the active ingredient to the agent.

Further provided is a method for treating or managing pain in a subject comprising administering to the subject the pharmaceutical composition as described herein, wherein the active ingredient is an oligonucleotide decoy comprising one or more binding sites for EGR1 and wherein the agent is a calcium ion.

BRIEF DESCRIPTION OF THE FIGURES

FIG. 1A: the clinical response score of each tested formulation was calculated as the total sum of clinical signs and displayed in a graph bar (maximum potential score=13, minimum potential score=0). FIGS. 1B and 1C present visual plots of the performance of the "saline+oligonucleotide" and the "1:0.0146 oligonucleotide:calcium" formulations, respectively. Each brown bar or surface on the plot marks the % of occurrence of a given clinical sign. Oligonucleotide molecular weight=14092.92 g/mol, $CaCl_2$ molecular weight=147.02 g/mol, single-strand=antisense strand of the double stranded oligonucleotide, oligonucleotides were injected at 100 mg/mL, N=2-6 rats per formulation, T-test, different from saline injection: $p<0.05$.

Figures 4A, 4B:
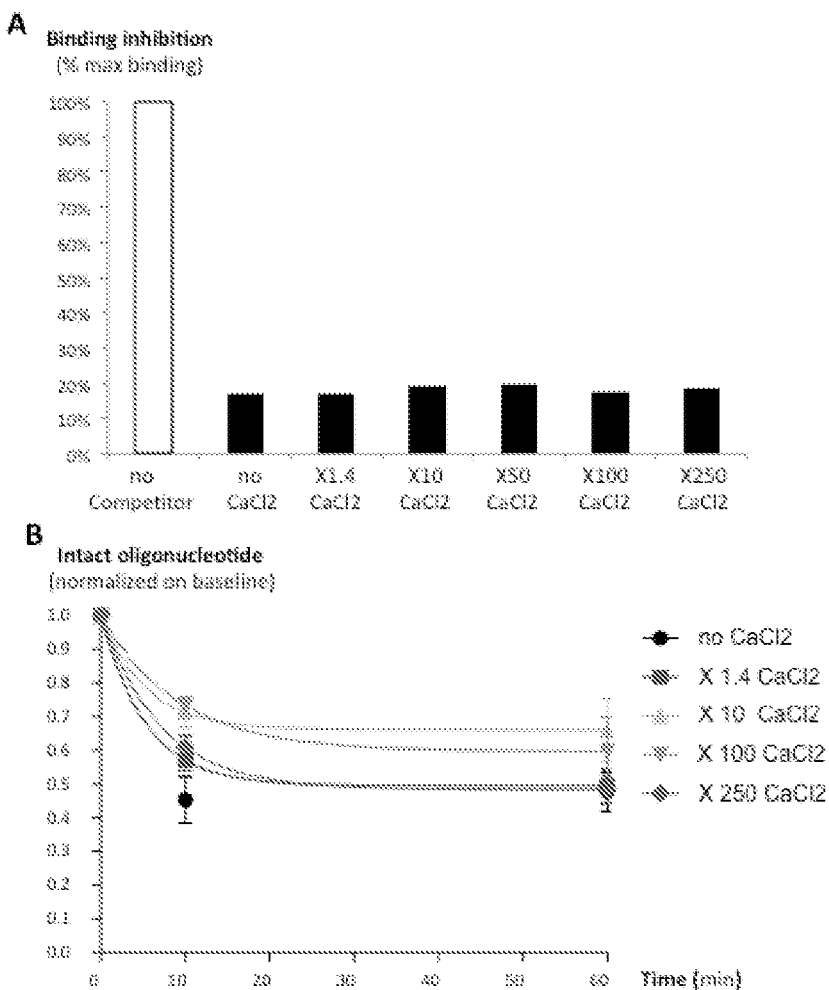

FIGS. 4A and 4B: oligonucleotide affinity and stability studies in the presence of calcium. FIG. 4A is a bar graph illustrating oligonucleotide binding affinity for its target, the transcription factor EGR1, as measured using a competition ELISA assay. A biotinylated EGR1 consensus tandem oligonucleotide (12 pmoles) was bound to the ELISA plate and incubated with nuclear protein extracts containing EGR1 in absence (white bar) or presence (black bars) of 100 pmoles of free competitor oligonucleotide including various excess molar ratios of CaCl$_2$ (X=CaCl$_2$ concentration/oligonucleotide concentration); FIG. 4B: oligonucleotide (4 µM) in the absence or presence of increasing excess molar ratios of CaCl$_2$ (X=CaCl$_2$ concentration/oligonucleotide concentration) was incubated in inactivated serum (Horse Serum, Heat Inactivated, Invitrogen) at 37° C. for 10 or 60 minutes. The quantity of intact oligonucleotide remaining following the incubation in the serum, which contains nucleases that degrade oligonucleotides, was measured using a gel electrophoresis and UV detection method. Data were normalized against the initial amount of oligonucleotide initially introduced in the solution.

Figures 5A, 5B:
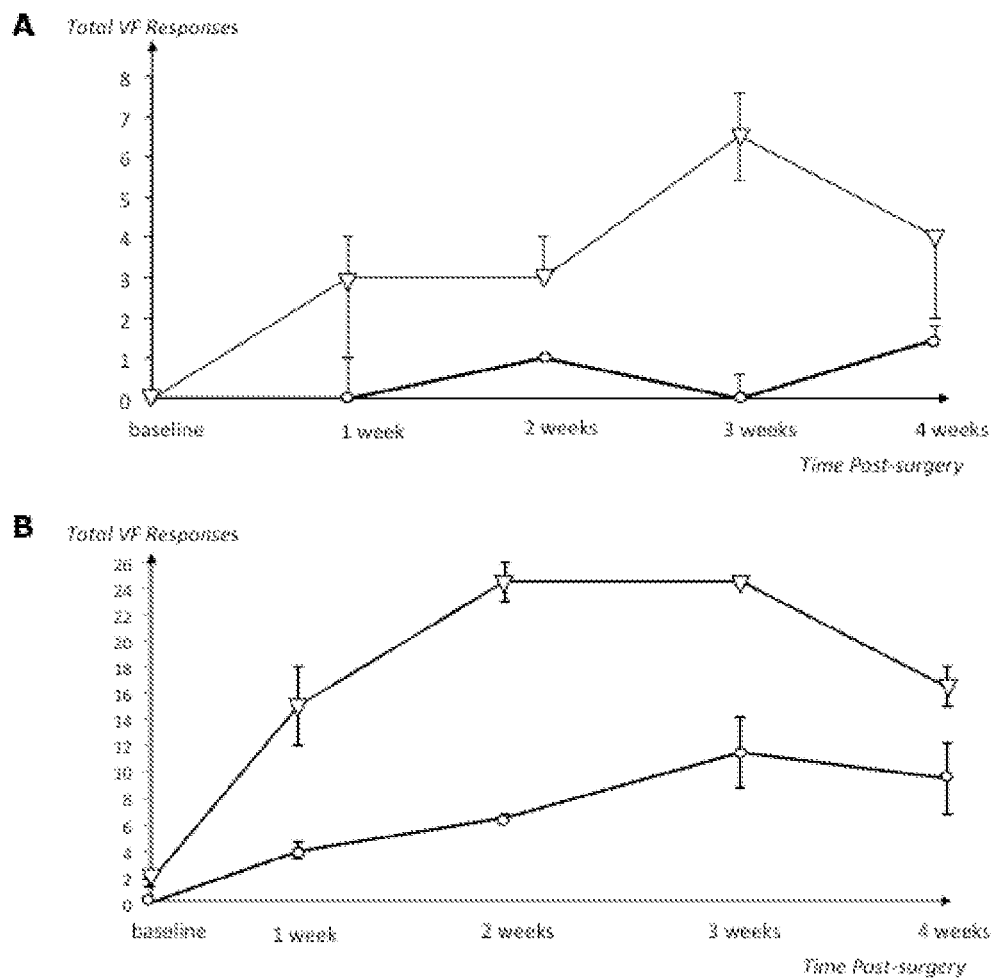

FIGS. 5A and 5B show the efficacy of a oligonucleotide for preventing pain in the spared nerve injury model of pain (Decosterd and Woolf, Pain 87:149-158 (2000)). Vehicle (triangle) or oligonucleotide (circle) were injected intrathecally (percutaneous, L5/6, 0.02 mL) once at the time of surgery. Pain was measured as mechanical hypersensitivity using Von Frey filaments (VF). Five repetitive applications for each of the following VF hair were performed on the paw ipsilateral to injury: 1-4-6-8-10 (twice)-26 gram. FIG. 5A: 1.4 mg of oligonucleotide without calcium vs. vehicle; FIG. 5B: 1.4 mg of oligonucleotide with CaCl$_2$ at the 1:0.0198 weight ratio vs. vehicle and buffered at pH 7.5 with Tris 10 mM. Median±40% and 60% percentiles values of total responses to repetitive VF stimulations are shown; N≥4 per group, T-test followed by a T-Welsh analysis, data distribution over the testing period, different from vehicle; p<0.01 in both studies.

DETAILED DESCRIPTION OF THE INVENTION

The present invention is based, in part, on the discovery that homeostatic levels of certain agents are important with respect to adverse effect(s) of a therapeutic entity, e.g., an active ingredient of a therapeutic entity. Accordingly the present invention provides compositions or formulations capable of inhibiting or reducing adverse effect(s) of a therapeutic entity. In addition, the present invention also provides methods of using the compositions or formulations for therapeutic treatments.

In one aspect, the present invention provides a composition, such as a pharmaceutical composition, comprising an active ingredient and an agent associated, directly or indirectly, with one or more adverse effect(s) of the active ingredient. In one embodiment, the agent is any entity, of which the homeostatic levels are directly or indirectly related to one or more adverse effect(s) of the active ingredient. In another embodiment, the agent is any entity, of which the homeostatic levels are changed, e.g., substantially upon administration of the active ingredient in vivo. In yet another embodiment, the agent is any entity, of which the homeostatic levels are sensitive to the administration of the active ingredient in vivo. In still another embodiment, the agent is any entity which is capable of interacting or interacts, directly or indirectly, with the active ingredient. In still yet another embodiment, the agent is any entity which is capable of binding or binds, directly or indirectly, with the active ingredient.

According to the present invention, the agent can be different, e.g., even with respect to the same active ingredient, depending on the tissue or cell type the active ingredient is administered into. In some embodiments, the agent is an ion. An ion can be an organic acid, such as malic, ascorbic, tartaric, lactic, acetic, formic, oxalic, or citric acid. In some embodiments, the agent is a metal ion, e.g., iron, zinc, copper, lead and nickel, etc. In some embodiments, the agent has a charge that is opposite of the net charge of the active ingredient. In some embodiments, the agent is a cation or anion. In some other embodiments, the agent is a calcium ion, a magnesium ion, or a potassium ion. In some other embodiments, the agent is an ion, carbohydrate (e.g., sugars, starches, etc.), lipid (e.g., saturated fatty acids, unsaturated fatty acids, triacylglycerols, glycerophospholipids, sphingolipids, and cholesterol, etc.), vitamin (e.g., selenium, zinc, vitamin A, thiamine, riboflavin, pyridoxin, niacin, pantothenic acid, cyanocobalamin, L-ascorbic acid and α-tocopherol, etc.), or alcohol (e.g., polyols such as glucose and mannitol, as well as, e.g., ethanol, etc.) or a combination thereof.

In yet further embodiments, the agent with respect to cerebrospinal fluid is an ion, e.g., calcium ions, magnesium ions or potassium ions. In still some other embodiments, the agent with respect to blood is one or more blood electrolytes and/or major constituents of extracellular, cellular and interstitial fluids. In some exemplary embodiments, the agent with respect to blood is Na$^+$, K$^+$, Ca$^{2+}$, Mg$^{2+}$, Cl$^-$, bicarbonates (e.g., HCO$_3^-$), phosphorus (e.g., HPO$_4^{2-}$), sulfates (e.g., SO$_4^{2-}$), organic acid, proteins, metal ions (iron, zinc, copper, lead and nickel, etc.), carbohydrates or alcohols (e.g., glucose, mannitol, ethanol), lipids, vitamins (e.g., selenium, zinc) or any combination thereof.

According to the present invention, the agent used in the composition of the active ingredient can be any amount suitable for the administration of the active ingredient in vivo, e.g., any amount that either inhibits or decreases one or more adverse effect(s) of the active ingredient without the agent. According to the present invention, one or more adverse effect(s) of the active ingredient includes any unwanted or undesirable effect produced as a result of in vivo administration of the active ingredient. An adverse effect can be any long term or short effect, local or systematic effect, or any effect associated with the toxicity of the active ingredient. Exemplary adverse effects include pain, headache, vomiting, arrhythmia, shivering, respiratory depression, dizziness, loss of motor control, lack of coordination, fatigue, memory impairment, rash, or numbness. In one embodiment, the adverse effect in the context of pain treatment with an oligonucleotide decoy can be relatively minor (e.g., light tail movement in a rodent or dog animal model) or more severe (e.g., a seizure), or may include muscle trembling, increased muscle tone in a limb, whole body rigidity, pain, or spontaneous vocalization.

In one embodiment, the agent used in the composition of the active ingredient is an in vivo stabilizing amount. As used herein, an "in vivo stabilizing amount" is an amount of the agent that upon administration along with the active ingredient does not cause any material or detectable change of the endogenous level, e.g., homeostatic level of the agent in vivo. Alternatively an "in vivo stabilizing amount" is an amount of the agent that upon administration along with the active ingredient inhibits or decreases one or more adverse effect(s) of the active ingredient without the agent. In some embodiments, the in vivo stabilizing amount of the agent is an amount that sufficiently saturates binding sites, e.g., available binding sites of the active ingredient to the agent. For example, the in vivo stabilizing amount of the agent can be an amount that capable of binding or binds to at least 0.001%, 0.1%, 0.5%, 1%, 2%, 5%, 10%, 20%, 30%, 40%, or 50% of binding sites, e.g., available binding sites of the active ingredient to the agent. In some other embodiments, the in vivo stabilizing amount of the agent is an amount that upon administration along with the active ingredient does not materially affect or cause detectable change of the pH (e.g., induces a change less than about 0.5 pH units, 0.2 pH units, 0.1 pH units, etc.) of the local site, tissue, or cell environment, etc.

In yet some other embodiments, the in vivo stabilizing amount of the agent is the amount that upon mixing with the active ingredient produces less than a predetermined level of free agent in the composition, e.g., minimum or undetectable level of free agent in the composition. For example, the predetermined level of free agent in the composition can be at least less than 0.1 mM, 0.5 mM, 1 mM, 1.5 mM, or 2 mM in a composition when the active ingredient is an oligonucleotide decoy and the agent is an ion, e.g., calcium. In another example, the predetermined level of the free agent in the composition is less than about 1%, 2%, 5%, 10%, 20%, 30%, 40%, 50%, 60%, 70%, 80%, 90% or 100% of the endogenous level, e.g., local concentration of the agent. In yet another example, the predetermined level of free agent in the composition is determined based on the saturation level of the binding sites in the active ingredient to the agent.

According to the present invention, the free agent is the agent that is not bound to the active ingredient, e.g., by electrostatic, covalent, or hydrophobic interactions, or any other mode of interaction. Alternatively the free agent is the agent that is capable of interfering or interferes with the endogenous level of the agent, e.g., systematically or at the local site of administration.

In still some other embodiments, the in vivo stabilizing amount of the agent is the amount that provide suitable ratio between the active ingredient and the agent so that when they are administered in vivo, it inhibits or decreases one or more adverse effect(s) of the active ingredient without the agent or alternatively it does not cause substantial or detectable change of endogenous level, e.g., homeostatic level of the agent. In some embodiments, the molar ratio or the weight ratio of the active ingredient to the agent ranges from about 1:1000 to about 1000:1. Non-limiting examples of ratios include 1:1, 1:5, 1:10, 1:50, 1:100, 1:250, 1:500, 1:1000, 1000:1, 500:1, 250:1, 100:1, 50:1, 10:1, 5:1, and any range derivable therein inclusive of fractions of integers (e.g., 100.5, 100.05, etc.). Further non-limiting examples of ratios include 1:1, 1:2, 1:3, 1:4, 1:5, 1:6, 1:7, 1:8, 1:9, 1:10, 10:1, 9:1, 8:1, 7:1, 6:1, 5:1, 4:1, 3:1, and 2:1, and any range derivable therein, inclusive of fractions of integers (e.g., 1.5, 1.05, etc.). In some embodiments, the active ingredient is a nucleic acid, such as an oligonucleotide (e.g., an oligonucleotide decoy), and the agent is a calcium ion, and wherein the weight ratio or the molar ratio of the active ingredient and the agent is from about 0.005 to 5, 0.05 to 5, 0.1 to 3, 0.2 to 2.8, 0.5 to 2, or 1 to 2. In some embodiments, the active ingredient is a nucleic acid, such as an oligonucleotide (e.g., an oligonucleotide decoy), and the agent is a calcium ion, and wherein the weight ratio or the molar ratio of the active ingredient and the agent is from about 1 to 0.001, 1 to 0.005, 1 to 0.01, 1 to 0.015, 1 to 0.018, 1 to 0.019, 1 to 0.02, 1 to 0.025, 1 to 0.03, 1 to 0.035, 1 to 0.4, or 1 to 0.5. For example, the weight ratio may be 1:1, 2:1, 4:1, 5:1, 15:1, 30:1, 50:1, 100:1, 200:1, 250:1, 300:1, 400:1, 500:1, or 1000:1. An agent, such as an ion (e.g., a calcium ion), can be comprised in a composition such as a salt (e.g., $CaCl_2$), and the molar amount or weight amount of that composition can be referenced in a ratio. Accordingly, in some embodiments, the agent is a calcium ion comprised in a composition such as $CaCl_2$, wherein the weight ratio of an active ingredient, such as a nucleic acid (e.g., an oligonucleotide, an oligonucleotide decoy) to the composition, e.g., $CaCl_2$, is about 1:1, 2:1, 4:1, 5:1, 15:1, 30:1, 50:1, 100:1, 200:1, 250:1, 300:1, 400:1, or 500:1, or any range derivable therein.

It is understood that the exact ratio of active ingredient to agent in a composition may vary, such as based on the chemical nature of the active ingredient (e.g., in the context of a nucleic acid, whether the nucleic acid is RNA, DNA, single stranded or double stranded, the percent GC content, or molecular weight), the agent and its local concentration (e.g., endogenous level) in the targeted in vivo site, and its intended delivery route. For example, in a environment with a higher endogenous calcium concentration, it is anticipated that the ratio of active ingredient (e.g., oligonucleotide decoy):calcium should be increased in a composition comprising such components.

In still yet some other embodiments, the in vivo stabilizing amount of the agent is the amount that when administered along with the active ingredient causes minimum, insubstantial, or undetectable amount of interaction, e.g., binding between the endogenous agent and the active ingredient.

According to the present invention, the active ingredient is any entity within a composition that provides intended activity of the composition. In some embodiments, the active ingredient is any therapeutically, prophylactically, or pharmacologically or physiologically active substance, or a mixture thereof. In general, an active ingredient is typically used in an amount sufficient to prevent, cure, diagnose or treat a disease or other condition, as the case may be. Non-limiting examples of active ingredients include nucleic acids, peptides, and small organic molecules. As used herein, a "small organic molecule" refers to a carbon-containing agent having a molecular weight of less than or equal to 1500 g/mol, such less than 1400, less than 1300, less than 1200, less than 1100, less than 1000, less than 900, less than 800, less than 700, less than 600, less than 500, less than 400, less than 300, less than 200, or less than 100 g/mol. In some embodiments, a small organic molecule excludes a polymer, such as a nucleic acid polymer (e.g., an oligonucleotide, polynucleotide, vector, etc.), a peptide, or a protein. In some embodiments, an active ingredient is a polymer, such as a nucleic acid polymer or a protein.

In some other embodiments, an active ingredient is an oligonucleotide. For example, an oligonucleotide can be an oligonucleotide decoy, such as described in U.S. Pat. Nos. 7,943,591 and 8,093,225. An "oligonucleotide decoy" refers to any double-stranded, nucleic acid-containing polymer generally less than approximately 200 nucleotides (or 100 base pairs) and including, but not limited to, DNA, RNA and RNA-DNA hybrids. The term encompasses sequences that include any of the known base analogs of DNA and RNA including, but not limited to, 2,6-diaminopurine, 5-carboxymethylaminomethyl-2-thiouracil, 5-carboxymethylaminomethyluracil, dihydrouracil, inosine, uracil-5-oxyacetic acid, N6-isopentenyladenine, 1-methyladenine, N-uracil-5-oxyacetic acid methylester, queosine, 2-thiocytosine, 5-bromouracil, methylphosphonate, phosphorodithioate, ormacetal, 3'-thioformacetal, nitroxide backbone, sulfone, sulfamate, morpholino derivatives, locked nucleic acid (LNA) derivatives, or peptide nucleic acid (PNA) derivatives. In some embodiments, the oligonucleotide decoy is composed of two complementary single-stranded oligonucleotides that are annealed together. In other embodiments, the oligonucleotide decoy is composed of one single-stranded oligonucleotide that forms intramolecular base pairs to create a substantially double-stranded structure.

In certain embodiments, the oligonucleotide decoys comprise one or more (e.g., 1, 2, 3, 4, 5, etc.) transcription factor binding sites. In related embodiments, each transcription factor binding site binds to a transcription factor selected from the group consisting of POU1F1, POU2F, POU3F, POU4F1, POU5F1, USF, EGR1, CREB/ATF, AP1, CEBP, SRF, ETS1, MEF2, SP1, RUNX, NFAT, ELK1, ternary complex factors, STAT, GATA1, ELF1, nuclear factor—granulocyte/macrophage a, HNF1, ZFHX3, IRF, TEAD1, TBP, NFY, caccc-box binding factors, KLF4, KLF7, IKZF, MAF, REST, HSF, KCNIP3 and PPAR transcription factors. In certain embodiments, transcription factor binding sites bind to two or more members of a family of closely-related transcription factors. Representative members of such transcription factor families can be selected from the group consisting of POU1F1, POU2F, POU3F, POU4F1, POU5F1, USF, EGR1, CREB/ATF, AP1, CEBP, SRF, ETS1, MEF2, SP1, RUNX, NFAT, ELK1, ternary complex factors, STAT, GATA1, ELF1, nuclear factor—granulocyte/macrophage a, HNF1, ZFHX3, IRF, TEAD1, TBP, NFY, caccc-box binding factors, KLF4, KLF7, IKZF, MAF, REST, HSF, KCNIP3 and PPAR transcription factors. Thus, in certain embodiments, an oligonucleotide decoy that binds to, e.g., EGR1, can also bind to one or more additional family members, e.g., EGR2, EGR3, EGR4.

In certain embodiments, the oligonucleotide decoys comprise two or more (e.g., 2, 3, 4, 5, etc.) transcription factor binding sites. In related embodiments, each transcription factor binding site binds to a transcription factor selected from the group consisting of POU1F1, POU2F, POU3F, POU4F1, POU5F1, USF, EGR1, CREB/ATF, AP1, CEBP, SRF, ETS1, MEF2, SP1, RUNX, NFAT, ELK1, ternary complex factors, STAT, GATA1, ELF1, nuclear factor—granulocyte/macrophage a, HNF1, ZFHX3, IRF, TEAD1, TBP, NFY, caccc-box binding factors, KLF4, KLF7, IKZF, MAF, REST, HSF, KCNIP3 and PPAR transcription factors. In certain embodiments, the relative position of the two or more transcription factor binding sites within the decoy modulates (e.g., increases or decreases) the binding affinity between a target transcription factor (i.e., the transcription factor that a particular binding site is designed to bind to) and its transcription factor binding site, e.g., as compared to the binding affinity between the transcription factor and a decoy having a single transcription factor binding site (e.g., a consensus binding site) specific to the transcription factor. Thus, the relative position of the two transcription factor binding sites within an oligonucleotide decoy of the invention can increase the affinity of the oligonucleotide decoy for a target transcription factor (e.g., for one or more of the transcription factors targeted by the decoy). In certain embodiments, the increase in affinity of the oligonucleotide decoy for a target transcription factor is 1.2 fold or greater (e.g., about 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 fold, or more). In certain embodiments, the relative position of the two transcription factor binding sites within an oligonucleotide decoy promotes protein-protein interactions between transcription factors bound to the sites, e.g., homodimerization or heterodimerization of the transcription factors. In certain embodiments, such protein-protein interactions between transcription factors stabilize their interactions, e.g., binding, to the oligonucleotide decoy, thereby increasing the binding affinity of the oligonucleotide decoy for one or more of the target transcription factors.

In certain embodiments, the transcription factor binding sites of an oligonucleotide decoy each bind to the same transcription factor, e.g., EGR1. In other embodiments, the transcription factor binding sites of an oligonucleotide decoy bind to different transcription factors, e.g., different members of a closely related family of transcription factors (e.g., different members of the EGR1 family) or a combination of transcription factors selected from the group consisting of POU1F1, POU2F, POU3F, POU4F1, POU5F1, USF, EGR1, CREB/ATF, AP1, CEBP, SRF, ETS1, MEF2, SP1, RUNX, NFAT, ELK1, ternary complex factors, STAT, GATA1, ELF1, nuclear factor—granulocyte/macrophage a, HNF1, ZFHX3, IRF, TEAD1, TBP, NFY, caccc-box binding factors, KLF4, KLF7, IKZF, MAF, REST, HSF, KCNIP3 and PPAR transcription factors.

In certain embodiments, the transcription factor binding sites of an oligonucleotide decoy are separated from each other by a linker sequence. Linker sequences can be 1, 2, 3, 4, 5, 6, 7, 8, 9, 10, or more base pairs in length. Typically, linker sequences will be two to five base pairs in length. In other embodiments, the transcription factor binding sites can be immediately adjacent to one another (e.g., no linker sequence is present) or overlapping. In cases where the transcription factor binding sites are overlapping, the transcription factor binding sites can share 1, 2, 3, 4, 5, or more base pairs. Alternatively, one or both of the transcription factor binding sites can be lacking base pairs that otherwise form part of a consensus binding sequence for the transcription factor(s) that bind to the site. In general, however, base pairs that are critical to the binding interaction between a transcription factor binding site and the transcription factors that bind to the site (e.g., base pairs that are essentially invariant in a consensus binding sequence for a particular transcription factor) are not shared or missing when transcription binding sequences are overlapping.

In certain embodiments, oligonucleotide decoys comprise flanking sequences located at each end of the decoy sequence. Flanking sequences can be 1, 2, 3, 4, 5, 6, or more base pairs in length. In general, flanking sequences are two to five base pairs in length. In preferred embodiments, 5' flanking sequences starts with a G/C base pair and 3' flanking sequences terminate in a G/C base pair. In preferred embodiments, flanking sequences do not form part of a transcription factor binding site or do not interact with or bind to transcription factors. In other embodiments, flanking sequences form weak interactions with transcription factors bound to an adjacent transcription factor binding site.

In certain embodiments, oligonucleotide decoys are generally at least 10, 11, 12, 13, 14, 15, or more base pairs in length. In related embodiments, oligonucleotide decoys are generally less than 65, 60, 55, 50, or 45 base pairs in length. In preferred embodiments, oligonucleotide decoys are about 20 to 40 base pairs in length. In other embodiments, oligonucleotide decoys are about 20 to 35, 25 to 40, or 25 to 35 base pairs in length.

In certain embodiments, the oligonucleotide decoys comprise: (a) a sequence selected from the group consisting of SEQ ID NOs.: 1-40, 42, 45 and 47-53; or (b) a sequence having at least 50%, 55%, 60%, 65%, 70%, 75%, 80%, 85%, 88%, 89%, 90%, 91%, 92%, 93%, 94%, 95%, 96%, 97%, 98%, or 99% identity with a sequence selected from the group consisting of SEQ ID NOs.: 1-40, 42, 45 and 47-53. In related embodiments, the oligonucleotide decoys comprise a sequence having at least 90% identity with a sequence selected from the group consisting of SEQ ID NOs.: 1-39, 42, 45 and 47-52. In other embodiments, the oligonucleotide decoys comprise a sequence having at least 85% identity with a sequence selected from the group consisting of SEQ ID NOs.: 1-17, 19-39, 42, 45 and 47-53. In other embodiments, the oligonucleotide decoys comprise a sequence having at least 80% identity with a sequence selected from the group consisting of SEQ ID NOs.: 1-5, 7-17, 19-39, 42, 45 and 47-53. In other embodiments, the oligonucleotide decoys comprise a sequence having at least 75% identity with a sequence selected from the group consisting of SEQ ID NOs.: 1-4, 7-9, 13, 15-17, 19-23, 26-39, 45, 48, 50, 51 and 53. In other embodiments, the oligonucleotide decoys comprise a sequence having at least 70% identity with a sequence selected from the group consisting of SEQ ID NOs.: 1-3, 7-9, 13, 15-17, 19-23, 26, 28, 30, 32, 34-36, 38-39 and 48. In other embodiments, the oligonucleotide decoys comprise a sequence having at least 65% identity with a sequence selected from the group consisting of SEQ ID NOs.: 2-3, 9, 13, 15-16, 19-23, 26, 28, 30, 32, 34-36, 38 and 39. In other embodiments, the oligonucleotide decoys comprise a sequence having at least 60% identity with a sequence selected from the group consisting of SEQ ID NOs.: 2, 13, 15-16, 21, 23, 26, 30, 32, 34-36, 38 and 39. In still other embodiments, the oligonucleotide decoys comprise a sequence having at least 55% identity with a sequence selected from the group consisting of SEQ ID NOs.: 16, 23, 30, 32, 34, 35, 38 and 39. In still other embodiments, the oligonucleotide decoys comprise a sequence having at least 50% identity with a sequence selected from the group consisting of SEQ ID NOs.: 30, 32, 35, and 38.

In certain embodiments, an oligonucleotide decoy comprises a double-stranded sequence represented by formula (1):

(1)
5'-$S_1n_2n_3n_4n_5A_6T_7D_8B_9N_{10}d_{11}d_{12}n_{13}n_{14}n_{15}n_{16}n_{17}A_{18}$ $T_{19}D_{20}$......$B_{21}N_{22}H_{23}H_{24}n_{25}n_{26}n_{27}n_{28}n_{29}n_{30}S_{31}$-3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "D" can be an A, G, or T nucleotide, "B" can be a C, G, or T nucleotide, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (1) has at least about 70%, 75%, 80%, 85%, 88%, 90%, 91%, 92%, 93%, 94%, 95%, 96%, 97%, 98%, or 99% sequence identity to the nucleotide sequence of SEQ ID NO.: 1. Such oligonucleotide decoys can bind to POU2F1 transcription factor. In certain embodiments, such oligonucleotide decoys can bind to one or more transcription factors closely related to POU2F1 transcription factor, such as POU2F2, POU3F1-2, and POU5F1.

In certain embodiments, an oligonucleotide decoy represented by formula (1) comprises a deletion of one or more (e.g., 1, 2, 3, 4, 5, 6, or 7) nucleotides selected from the group consisting of $d_{11}$, $d_{12}$, $n_{13}$, $n_{14}$, $n_{15}$, $n_{16}$, and $n_{17}$. In certain embodiments, oligonucleotide decoys comprising a deletion of one or more nucleotides selected from the group consisting of $d_{11}$, $d_{12}$, $n_{13}$, $n_{14}$, $n_{15}$, $n_{16}$, and $n_{17}$ have at least 70% identity to the nucleotide sequence of SEQ ID NO.: 1.

In certain embodiments, an oligonucleotide decoy comprises a double-stranded sequence represented by formula (2):

(2)
5'-$S_1n_2n_3n_4n_5n_6Y_7C_8V_9Y_{10}R_{11}N_{12}G_{13}n_{14}n_{15}c_{16}v_{17}y_{18}$ $d_{19}b_{20}$......$g_{21}y_{22}C_{23}V_{24}Y_{25}R_{26}B_{27}G_{28}R_{29}n_{30}n_{31}n_{32}$ $n_{33}n_{34}n_{35}S_{36}$-3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "D" can be an A, G, or T nucleotide, "B" can be a C, G, or T nucleotide, "R" can be a G or an A, "V" can be an A, C, or G, "Y" can be a C or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (2) has at least about 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 2. Such oligonucleotide decoys can bind to USF1 transcription factor. In certain embodiments, such oligonucleotide decoys can bind to one or more transcription factors closely related to USF1 transcription factor, such as USF2.

In certain embodiments, an oligonucleotide decoy represented by formula (2) comprises a deletion of one or more (e.g., 1, 2, 3, 4, 5, 6, 7, 8 or 9) nucleotides selected from the group consisting of $n_{14}$, $n_{15}$, $c_{16}$, $v_{17}$, $y_{18}$, $d_{19}$, $b_{20}$, $g_{21}$, and $y_{22}$. In certain embodiments, oligonucleotide decoys comprising a deletion of one or more nucleotides selected from the group consisting of $n_{14}$, $n_{15}$, $c_{16}$, $v_{17}$, $y_{18}$, $d_{19}$, $b_{20}$, $g_{21}$, and $y_{22}$ have at least 60% identity to the nucleotide sequence of SEQ ID NO.: 2.

In certain embodiments, an oligonucleotide decoy comprises a double-stranded sequence represented by formula (3):

(3)
5'-$S_1n_2n_3W_4W_5G_6S_7G_8K_9R_{10}G_{11}G_{12}M_{13}n_{14}n_{15}n_{16}w_{17}w_{18}$ $w_{19}g_{20}$ . . . . . . $s_{21}g_{22}K_{23}R_{24}G_{25}G_{26}M_{27}D_{28}$ $n_{29}n_{30}n_{31}n_{32}n_{33}S_{34}$-3' wherein "A" is an adenine nucleotide, "C" is a cytosine nucleotide, "G" is a guanine nucleotide, "T" is a thymine nucleotide, "S" can be a G or C nucleotide, "N" can be any nucleotide, 'W' can be an A or a T, "D" can be an A, G, or T nucleotide, "R" can be a G or an A, "K" can be a T or a G, "M" can be a C or an A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (3) has at least about 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 3. Such oligonucleotide decoys can bind to EGR1 transcription factor. In certain embodiments, such oligonucleotide decoys can bind to one or more transcription factors closely related to EGR1 transcription factor, such as EGR2-4.

In certain embodiments, an oligonucleotide decoy represented by formula (3) comprises a deletion of one or more (e.g., 1, 2, 3, 4, 5, 6, 7, 8 or 9) nucleotides selected from the group consisting of $n_{14}$, $n_{15}$, $n_{16}$, $w_{17}$, $w_{18}$, $w_{19}$, $g_{20}$, $s_{21}$, and $g_{22}$. In certain embodiments, oligonucleotide decoys comprising a deletion of one or more nucleotides selected from the group consisting of $n_{14}$, $n_{15}$, $n_{16}$, $w_{17}$, $w_{18}$, $w_{19}$, $g_{20}$, $s_{21}$, and $g_{22}$ have at least 65% identity to the nucleotide sequence of SEQ ID NO.: 3.

In certain embodiments, an oligonucleotide decoy comprises a double-stranded sequence represented by formula (4):

(4)
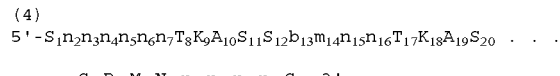

wherein "A" is an adenine nucleotide, "C" is a cytosine nucleotide, "G" is a guanine nucleotide, "T" is a thymine nucleotide, "S" can be a G or C nucleotide, "N" can be any nucleotide, "B" can be a C, G or T, "K" can be a T or a G, "M" can be a C or an A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (4) has at least about 75%, 80%, 85%, 88%, 90%, 91%, 92%, 93%, 94%, 95%, 96%, 97%, 98%, or 99% sequence identity to the nucleotide sequence of SEQ ID NO.: 4. Such oligonucleotide decoys can bind to CREB1 transcription factor. In certain embodiments, such oligonucleotide decoys can bind to one or more transcription factors closely related to CREB1 transcription factor, such as CREB3-5 and ATF1-7.

In certain embodiments, an oligonucleotide decoy represented by formula (4) comprises a deletion of one or more (e.g., 1, 2, 3 or 4) nucleotides selected from the group consisting of $b_{13}$, $m_{14}$, $n_{15}$, and $n_{16}$. In certain embodiments, oligonucleotide decoys comprising a deletion of one or more nucleotides selected from the group consisting of $b_{13}$, $m_{14}$, $n_{15}$, and $n_{16}$ have at least 75% identity to the nucleotide sequence of SEQ ID NO.: 4.

In certain embodiments, an oligonucleotide decoy comprises a double-stranded sequence represented by formula (5):

(5)
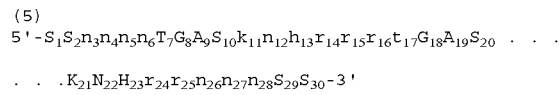

wherein "A" is an adenine nucleotide, "C" is a cytosine nucleotide, "G" is a guanine nucleotide, "T" is a thymine nucleotide, "S" can be a G or C nucleotide, "N" can be any nucleotide, "R" can be a G or an A, "K" can be a T or a G, "H" can be a C, T or an A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (5) has at least about 80%, 85%, 88%, 90%, 91%, 92%, 93%, 94%, 95%, 96%, 97%, 98%, or 99% sequence identity to the nucleotide sequence of SEQ ID NO.: 5. Such oligonucleotide decoys can bind to AP1/JUN transcription factors. In certain embodiments, such oligonucleotide decoys can bind to one or more transcription factors closely related to AP1/JUN transcription factors, such as AP1/JUN-B, -D and AP1/FOS.

In certain embodiments, an oligonucleotide decoy represented by formula (5) comprises a deletion of one or more (e.g., 1, 2, 3, 4, 5, 6 or 7) nucleotides selected from the group consisting of $k_{11}$, $n_{12}$, $h_{13}$, $r_{14}$, $r_{15}$, $r_{16}$, and $t_{17}$. In certain embodiments, oligonucleotide decoys comprising a deletion of one or more nucleotides selected from the group consisting of $k_{11}$, $n_{12}$, $h_{13}$, $r_{14}$, $r_{15}$, $r_{16}$, and $t_{17}$ have at least 80% identity to the nucleotide sequence of SEQ ID NO.: 5.

In certain embodiments, an oligonucleotide decoy comprises a double-stranded sequence represented by formula (6):

(6)
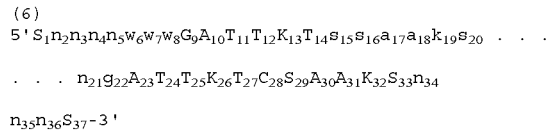

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be A or T, "K" can be a T or a G, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (6) has at least about 85%, 88%, 90%, 91%, 92%, 93%, 94%, 95%, 96%, 97%, 98%, or 99% sequence identity to the nucleotide sequence of SEQ ID NO.: 6. Such oligonucleotide decoys can bind to CEBPA transcription factor. In certain embodiments, such oligonucleotide decoys can bind to one or more transcription factors closely related to CEBPA transcription factor, such as CEBP-B, -D, -E, -G, -Z.

In certain embodiments, an oligonucleotide decoy represented by formula (6) comprises a deletion of one or more (e.g., 1, 2, 3, 4, 5, 6, 7 or 8) nucleotides selected from the group consisting of $s_{15}$, $s_{16}$, $a_{17}$, $a_{18}$, $k_{19}$, $s_{20}$, $n_{21}$, and $g_{22}$. In certain embodiments, oligonucleotide decoys comprising a deletion of one or more nucleotides selected from the group consisting of $s_{15}$, $s_{16}$, $a_{17}$, $a_{18}$, $k_{19}$, $s_{20}$, $n_{21}$, and $g_{22}$ have at least 85% identity to the nucleotide sequence of SEQ ID NO.: 6.

In certain embodiments, an oligonucleotide decoy comprises a double-stranded sequence represented by formula (7):

(7)
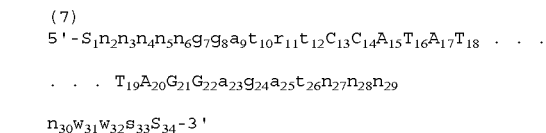

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or T, Y can be a C or T, "R" can be a G or A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (7) has at least about 70%, 75%, 80%, 85%, 88%, 90%, 91%, 92%, 93%, 94%, 95%, 96%, 97%, 98%, or 99% sequence identity to the nucleotide sequence of SEQ ID NO.: 7. Such oligonucleotide decoys can bind to SRF transcription factor. In certain embodiments, such oligonucleotide decoys can bind to one or more transcription factors closely related to SRF transcription factor, such as ELK1.

In certain embodiments, an oligonucleotide decoy represented by formula (7) comprises a deletion of one or more (e.g., 1, 2, 3, 4, 5, 6, 7, 8, 9, 10, 11, 12, 13, 14, 15, 16 or 17) nucleotides selected from the group consisting of $g_7$, $g_8$, $a_9$, $t_{10}$, $r_{11}$, $t_{12}$, $a_{23}$, $g_{24}$, $a_{25}$, $t_{26}$, $n_{27}$, $n_{28}$, $n_{29}$, $n_{30}$, $w_{31}$, $w_{32}$ and $s_{33}$. In certain embodiments, oligonucleotide decoys comprising a deletion of one or more nucleotides selected from the group consisting of $g_7$, $g_8$, $a_9$, $t_{10}$, $r_{11}$, $t_{12}$, $a_{23}$, $g_{24}$, $a_{25}$, $t_{26}$, $n_{27}$, $n_{28}$, $n_{29}$, $n_{30}$, $w_{31}$, $w_{32}$ and $s_{33}$ have at least 70% identity to the nucleotide sequence of SEQ ID NO.: 7.

In certain embodiments, an oligonucleotide decoy comprises a double-stranded sequence represented by formula (8):

(8)
5'-$S_1 n_2 n_3 n_4 n_5 C_6 A_7 G_8 G_9 A_{10} d_{11} d_{12} d_{13} d_{14} d_{15} d_{16} d_{17} d_{18} d_{19} T_{20}$ . . .

. . . $C_{21} C_{22} A_{23} T_{24} A_{25} T_{26} T_{27} A_{28} G_{29} n_{30} n_{31} n_{32} n_{33} S_{34}$-3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "D" can be an A, T or G, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (8) has at least about 70%, 75%, 80%, 85%, 88%, 90%, 91%, 92%, 93%, 94%, 95%, 96%, 97%, 98%, or 99% sequence identity to the nucleotide sequence of SEQ ID NO.: 8. Such oligonucleotide decoys can bind to SRF transcription factor. In certain embodiments, such oligonucleotide decoys can bind to one or more transcription factors closely related to SRF transcription factor, such as ETS1.

In certain embodiments, an oligonucleotide decoy represented by formula (8) comprises a deletion of one or more (e.g., 1, 2, 3, 4, 5, 6, 7, 8 or 9) nucleotides selected from the group consisting of $d_{11}$, $d_{12}$, $d_{13}$, $d_{14}$, $d_{15}$, $d_{16}$, $d_{17}$, $d_{18}$ and $d_{19}$. In certain embodiments, oligonucleotide decoys comprising a deletion of one or more nucleotides selected from the group consisting of $d_{11}$, $d_{12}$, $d_{13}$, $d_{14}$, $d_{15}$, $d_{16}$, $d_{17}$, $d_{18}$ and $d_{19}$ have at least 70% identity to the nucleotide sequence of SEQ ID NO.: 8.

In certain embodiments, an oligonucleotide decoy comprises a double-stranded sequence represented by formula (9):

(9)
5'-$S_1 n_2 n_3 n_4 n_5 C_6 T_7 A_8 W_9 A_{10} M_{11} W_{12} T_{13} A_{14} A_{15} n_{16} n_{17} n_{18} n_{19} C_{20}$ . . .

. . . $t_{21} A_{22} W_{23} A_{24} A_{25} A_{26} T_{27} A_{28} A_{29} A_{30} A_{31} n_{32} n_{33} n_{34} S_{35}$-3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or an T, "M" can be a C or an A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (9) has at least about 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 9. Such oligonucleotide decoys can bind to MEF2A transcription factor. In certain embodiments, such oligonucleotide decoys can bind to one or more transcription factors closely related to MEF2A transcription factor, such as MEF2B-C.

In certain embodiments, an oligonucleotide decoy represented by formula (9) comprises a deletion of one or more (e.g., 1, 2, 3, 4, 5 or 6) nucleotides selected from the group consisting of $n_{16}$, $n_{17}$, $n_{18}$, $n_{19}$, $c_{20}$ and $t_{21}$. In certain embodiments, oligonucleotide decoys comprising a deletion of one or more nucleotides selected from the group consisting of $n_{16}$, $n_{17}$, $n_{18}$, $n_{19}$, $c_{20}$ and $t_{21}$ have at least 65% identity to the nucleotide sequence of SEQ ID NO.: 9.

In certain embodiments, an oligonucleotide decoy comprises a double-stranded sequence represented by formula (10):

(10)
5'-$n_1 n_2 n_3 n_4 R_5 R_6 G_7 S_8 C_9 S_{10} K_{11} r_{12} r_{13} n_{14} n_{15} n_{16} r_{17} r_{18} G_{19} S_{20}$ . . .

. . . $C_{21} K_{22} R_{23} R_{24} N_{25} n_{26} n_{27} n_{28} n_{29} n_{30}$-3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "K" can be a T or a G, "R" can be a G or an A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (10) has at least about 80%, 85%, 88%, 90%, 91%, 92%, 93%, 94%, 95%, 96%, 97%, 98%, or 99% sequence identity to the nucleotide sequence of SEQ ID NO.: 10. Such oligonucleotide decoys can bind to SP1 transcription factor. In certain embodiments, such oligonucleotide decoys can bind to one or more transcription factors closely related to SP1 transcription factor, such as SP2-8.

In certain embodiments, an oligonucleotide decoy represented by formula (10) comprises a deletion of one or more (e.g., 1, 2, 3, 4, 5, 6 or 7) nucleotides selected from the group consisting of $r_{12}$, $r_{13}$, $n_{14}$, $n_{15}$, $n_{16}$, $r_{17}$, and $r_{18}$. In certain embodiments, oligonucleotide decoys comprising a deletion of one or more nucleotides selected from the group consisting of $n_{16}$, $n_{17}$, $n_{18}$, $n_{19}$, $c_{20}$ and $t_{21}$ have at least 80% identity to the nucleotide sequence of SEQ ID NO.: 10.

In certain embodiments, an oligonucleotide decoy comprises a double-stranded sequence represented by formula (11):

(11)

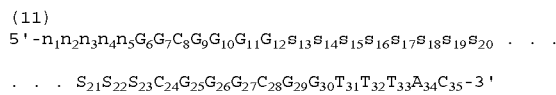

wherein "A" is an adenine nucleotide, "C" is a cytosine nucleotide, "G" is a guanine nucleotide, "T" is a thymine nucleotide, "S" can be a G or C nucleotide, "N" can be any nucleotide, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (11) has at least about 80%, 85%, 88%, 90%, 91%, 92%, 93%, 94%, 95%, 96%, 97%, 98%, or 99% sequence identity to the nucleotide sequence of SEQ ID NO.: 11. Such oligonucleotide decoys can bind to SP 1 transcription factor. In certain embodiments, such oligonucleotide decoys can bind to one or more transcription factors closely related to SP1 transcription factor, such as SP2-8.

In certain embodiments, an oligonucleotide decoy represented by formula (11) comprises a deletion of one or more (e.g., 1, 2, 3, 4, 5, 6, 7, 8, 9, 10 or 11) nucleotides selected from the group consisting of $s_{13}$ $s_{14}$, $s_{15}$, $s_{16}$, $s_{17}$, $s_{18}$, $s_{19}$, $s_{20}$, $s_{21}$, $s_{22}$, and $s_{23}$. In certain embodiments, oligonucleotide decoys comprising a deletion of one or more nucleotides selected from the group consisting of $s_{13}$, $s_{14}$ $s_{15}$, $s_{16}$, $s_{17}$, $s_{18}$, $s_{19}$, $s_{20}$, $s_{21}$, $s_{22}$, and $s_{23}$ have at least 80% identity to the nucleotide sequence of SEQ ID NO.: 11.

In certain embodiments, an oligonucleotide decoy comprises a double-stranded sequence represented by formula (12):

(12)

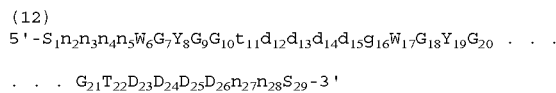

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or a T, Y can be a C or a T, "D" can be an A, T or a G, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (12) has at least about 80%, 85%, 88%, 90%, 91%, 92%, 93%, 94%, 95%, 96%, 97%, 98%, or 99% sequence identity to the nucleotide sequence of SEQ ID NO.: 12. Such oligonucleotide decoys can bind to RUNX1 transcription factor. In certain embodiments, such oligonucleotide decoys can bind to one or more transcription factors closely related to RUNX1 transcription factor, such as RUNX2-3.

In certain embodiments, an oligonucleotide decoy represented by formula (12) comprises a deletion of one or more (e.g., 1, 2, 3, 4, 5 or 6) nucleotides selected from the group consisting of $t_{11}$, $h_{12}$, $h_{13}$, $h_{14}$, $h_{15}$, and $g_{16}$. In certain embodiments, oligonucleotide decoys comprising a deletion of one or more nucleotides selected from the group consisting of $t_{11}$, $h_{12}$, $h_{13}$, $h_{14}$, $h_{15}$, and $g_{16}$ have at least 80% identity to the nucleotide sequence of SEQ ID NO.: 12.

In certain embodiments, an oligonucleotide decoy comprises a double-stranded sequence represented by formula (13):

(13)

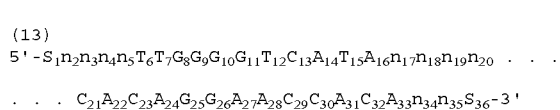

wherein "A" is an adenine nucleotide, "C" is a cytosine nucleotide, "G" is a guanine nucleotide, "T" is a thymine nucleotide, "S" can be a G or C nucleotide, "N" can be any nucleotide, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (13) has at least about 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 13. Such oligonucleotide decoys can bind to RUNX1 transcription factor. In certain embodiments, such oligonucleotide decoys can bind to one or more transcription factors closely related to RUNX1 transcription factor, such as RUNX2-3.

In certain embodiments, an oligonucleotide decoy represented by formula (13) comprises a deletion of one or more (e.g., 1, 2, 3 or 4) nucleotides selected from the group consisting of $n_{17}$, $n_{18}$, $n_{19}$ and $n_{20}$. In certain embodiments, oligonucleotide decoys comprising a deletion of one or more nucleotides selected from the group consisting of $n_{17}$, $n_{18}$, $n_{19}$ and $n_{20}$ have at least 60% identity to the nucleotide sequence of SEQ ID NO.: 13.

In certain embodiments, an oligonucleotide decoy comprises a double-stranded sequence represented by formula (14):

(14)

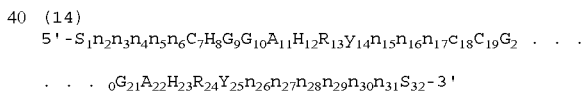

wherein "A" is an adenine nucleotide, "C" is a cytosine nucleotide, "G" is a guanine nucleotide, "T" is a thymine nucleotide, "S" can be a G or C nucleotide, "N" can be any nucleotide, "R" can be G or A, "H" can be A, T or C, "Y" can be a C or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (14) has at least about 80%, 85%, 88%, 90%, 91%, 92%, 93%, 94%, 95%, 96%, 97%, 98%, or 99% sequence identity to the nucleotide sequence of SEQ ID NO.: 14. Such oligonucleotide decoys can bind to ETS1 transcription factor. In certain embodiments, such oligonucleotide decoys can bind to one or more transcription factors closely related to ETS1 transcription factor, such as ELK1.

In certain embodiments, an oligonucleotide decoy represented by formula (14) comprises a deletion of one or more (e.g., 1, 2, 3, 4 or 5) nucleotides selected from the group consisting of $y_{14}$, $n_{15}$ $n_{16}$, $n_{17}$ and $c_{18}$. In certain embodiments, oligonucleotide decoys comprising a deletion of one or more nucleotides selected from the group consisting of $y_{14}$, $n_{15}$, $n_{16}$, $n_{17}$ and $c_{18}$ have at least 80% identity to the nucleotide sequence of SEQ ID NO.: 14.

In certain embodiments, an oligonucleotide decoy comprises a double-stranded sequence represented by formula (15):

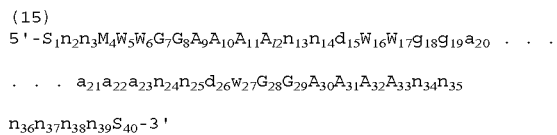

wherein "A" is an adenine nucleotide, "C" is a cytosine nucleotide, "G" is a guanine nucleotide, "T" is a thymine nucleotide, "S" can be a G or C nucleotide, "N" can be any nucleotide, "D" can be an A, G or a T, "W" can be an A or a T, "M" can be C or A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (15) has at least about 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 15. Such oligonucleotide decoys can bind to NFATC1 transcription factor. In certain embodiments, such oligonucleotide decoys can bind to one or more transcription factors closely related to NFATC1 transcription factor, such as NFATC2-4.

In certain embodiments, an oligonucleotide decoy represented by formula (15) comprises a deletion of one or more (e.g., 1, 2, 3, 4, 5, 6, 7, 8, 9, 10, 11, 12, 13, 14 or 15) nucleotides selected from the group consisting of $n_{13}$, $n_{14}$, $d_{15}$, $w_{16}$, $w_{17}$, $g_{18}$, $g_{19}$, $a_{20}$, $a_{21}$, $a_{22}$, $a_{23}$, $n_{24}$, $n_{25}$, $d_{26}$ and $w_{27}$. In certain embodiments, oligonucleotide decoys comprising a deletion of one or more nucleotides selected from the group consisting of $n_{13}$, $n_{14}$, $d_{15}$, $w_{16}$, $w_{17}$, $g_{18}$, $g_{19}$, $a_{20}$, $a_{21}$, $a_{22}$, $a_{23}$, $n_{24}$, $n_{25}$, $d_{26}$ and $w_{27}$ have at least 60% identity to the nucleotide sequence of SEQ ID NO.: 15.

In certain embodiments, an oligonucleotide decoy comprises a double-stranded sequence represented by formula (16):

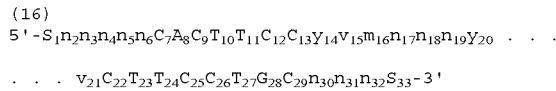

wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "V" can be G, A or C, "M" can be C or A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (16) has at least about 55%, 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 16. Such oligonucleotide decoys can bind to ELK1 transcription factor. In certain embodiments, such oligonucleotide decoys can bind to one or more transcription factors closely related to ELK1 transcription factor, such as ETS1.

In certain embodiments, an oligonucleotide decoy represented by formula (16) comprises a deletion of one or more (e.g., 1, 2, 3, 4, 5, 6, 7 or 8) nucleotides selected from the group consisting of $y_{14}$, $v_{15}$, $m_{16}$, $n_{17}$, $n_{18}$, $n_{19}$, $y_{20}$ and $v_{21}$. In certain embodiments, oligonucleotide decoys comprising a deletion of one or more nucleotides selected from the group consisting of $y_{14}$, $v_{15}$, $m_{16}$, $n_{17}$, $n_{18}$, $n_{19}$, $y_{20}$ and $v_{21}$ have at least 55% identity to the nucleotide sequence of SEQ ID NO.: 16.

In certain embodiments, an oligonucleotide decoy comprises a double-stranded sequence represented by formula (17):

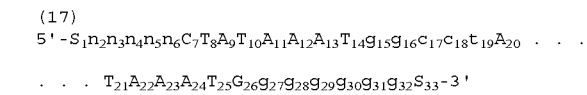

wherein "A" is an adenine nucleotide, "C" is a cytosine nucleotide, "G" is a guanine nucleotide, "T" is a thymine nucleotide, "S" can be a G or C nucleotide, "N" can be any nucleotide, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (17) has at least about 70%, 75%, 80%, 85%, 88%, 90%, 91%, 92%, 93%, 94%, 95%, 96%, 97%, 98%, or 99% sequence identity to the nucleotide sequence of SEQ ID NO.: 17. Such oligonucleotide decoys can bind to ternary complex factors. In certain embodiments, such oligonucleotide decoys can bind to one or more transcription factors closely related to ternary complex factors, such as SRF.

In certain embodiments, an oligonucleotide decoy represented by formula (17) comprises a deletion of one or more (e.g., 1, 2, 3, 4 or 5) nucleotides selected from the group consisting of $g_{15}$, $g_{16}$, $c_{17}$, $c_{18}$ and $t_{19}$. In certain embodiments, oligonucleotide decoys comprising a deletion of one or more nucleotides selected from the group consisting of $g_{15}$, $g_{16}$, $c_{17}$, $c_{18}$ and $t_{19}$ have at least 70% identity to the nucleotide sequence of SEQ ID NO.: 17.

In certain embodiments, an oligonucleotide decoy comprises a double-stranded sequence represented by formula (18):

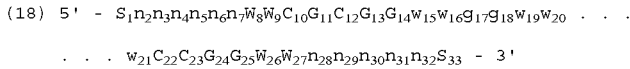

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can an A or a T, lower case letters can optionally be deleted, and the numbers in subscript represent the position of a nucleotide in the sequence. Although the formula shows a single strand, it should be understood that a complementary strand is included as part of the structure.

In preferred embodiments, an oligonucleotide decoy having a sequence represented by formula (18) has at least 90%, 91%, 92%, 93%, 94%, 95%, 96%, 97%, 98%, or 99% sequence identity to the nucleotide sequence of SEQ ID NO.: 18. Such oligonucleotide decoys can bind to STAT1 transcription factor. In certain embodiments, such oligonucleotide decoys can bind to one or more transcription factors closely related to STAT1 transcription factor, such as STAT2-6.

In certain embodiments, an oligonucleotide decoy represented by formula (18) comprises a deletion of one or more (e.g., 1, 2, 3, 4, 5, 6 or 7) nucleotides selected from the group consisting of $w_{15}$, $w_{16}$, $g_{17}$, $g_{18}$, $w_{19}$, $w_{20}$ and $w_{21}$. In certain embodiments, oligonucleotide decoys comprising a deletion of one or more nucleotides selected from the group consisting of $w_{15}$, $w_{16}$, $g_{17}$, $g_{18}$, $w_{19}$, $w_{20}$ and $w_{21}$ have at least 90% identity to the nucleotide sequence of SEQ ID NO.: 18.

In certain embodiments, an oligonucleotide decoy comprises a double-stranded sequence represented by formula (19):

(19) 5' - $S_1n_2n_3n_4T_5G_6C_7C_8T_9T_{10}A_{11}T_{12}C_{13}T_{14}c_{15}t_{16}n_{17}n_{18}g_{19}g_{20}$ . . .

. . . $G_{21}A_{22}T_{23}A_{24}A_{25}S_{26}n_{27}n_{28}n_{29}n_{30}S_{31}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (19) has at least about 65%, 70%, 75%, 80%, 85%, 90%, 91%, 92%, 93%, 94%, 95%, 96%, 97%, 98%, or 99% sequence identity to the nucleotide sequence of SEQ ID NO.: 19. Such oligonucleotide decoys can bind to GATA1 transcription factor. In certain embodiments, such oligonucleotide decoys can bind to one or more transcription factors closely related to GATA1 transcription factor, such as GATA2-4.

In certain embodiments, an oligonucleotide decoy represented by formula (19) comprises a deletion of one or more (e.g., 1, 2, 3, 4, 5 or 6) nucleotides selected from the group consisting of $c_{15}$, $t_{16}$, $n_{17}$, $n_{18}$, $g_{19}$ and $g_{20}$. In certain embodiments, oligonucleotide decoys comprising a deletion of one or more nucleotides selected from the group consisting of $c_{15}$, $t_{16}$, $n_{17}$, $n_{18}$, $g_{19}$ and $g_{20}$ have at least 65% identity to the nucleotide sequence of SEQ ID NO.: 19.

In certain embodiments, an oligonucleotide decoy comprises a double-stranded sequence represented by formula (20):

(20) 5' - $S_1n_2n_3n_4n_5n_6T_7G_8A_9A_{10}T_{11}w_{12}w_{13}g_{14}a_{15}g_{16}g_{17}a_{18}a_{19}a_{20}$ . . .

. . . $a_{21}w_{22}w_{23}G_{24}C_{25}A_{26}T_{27}G_{28}C_{29}n_{30}n_{31}S_{32}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can an A or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (20) has at least about 65%, 70%, 75%, 80%, 85%, 90%, 91%, 92%, 93%, 94%, 95%, 96%, 97%, 98%, or 99% sequence identity to the nucleotide sequence of SEQ ID NO.: 20. Such oligonucleotide decoys can bind to ELF1 transcription factor. In certain embodiments, such oligonucleotide decoys can bind to one or more transcription factors closely related to ELF1 transcription factor, such as POU1F1.

In certain embodiments, an oligonucleotide decoy represented by formula (20) comprises a deletion of one or more (e.g., 1, 2, 3, 4, 5, 6, 7, 8, 9, 10, 11 or 12) nucleotides selected from the group consisting of $w_{12}$, $w_{13}$, $g_{14}$, $a_{15}$, $g_{16}$, $g_{17}$, $a_{15}$, $a_{19}$, $a_{20}$, $a_{21}$, $w_{22}$ and $w_{23}$. In certain embodiments, oligonucleotide decoys comprising a deletion of one or more nucleotides selected from the group consisting of $w_{12}$, $w_{13}$, $g_{14}$, $a_{15}$, $g_{16}$, $g_{17}$, $a_{18}$, $a_{19}$, $a_{20}$, $a_{21}$, $w_{22}$ and $w_{23}$ have at least 65% identity to the nucleotide sequence of SEQ ID NO.: 20

In certain embodiments, an oligonucleotide decoy comprises a double-stranded sequence represented by formula (21):

(21) 5' - $S_1n_2n_3n_4n_5G_6A_7G_8A_9T_{10}T_{11}k_{12}c_{13}a_{14}c_{15}n_{16}n_{17}n_{18}g_{19}a_{20}$ . . .

. . . $g_{21}a_{22}t_{23}T_{24}K_{25}C_{26}A_{27}C_{28}n_{29}n_{30}n_{31}n_{32}S_{33}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "K" can be a G or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (21) has at least about 60%, 65%, 70%, 75%, 80%, 85%, 90%, 91%, 92%, 93%, 94%, 95%, 96%, 97%, 98%, or 99% sequence identity to the nucleotide sequence of SEQ ID NO.: 21. Such oligonucleotide decoys can bind to "nuclear factor—granulocyte/macrophage a" transcription factors. In certain embodiments, such oligonucleotide decoys can bind to one or more transcription factors closely related to "nuclear factor—granulocyte/macrophage a" transcription factors, such as "nuclear factor—granulocyte/macrophage b-c".

In certain embodiments, an oligonucleotide decoy represented by formula (21) comprises a deletion of one or more (e.g., 1, 2, 3, 4, 5, 6, 7, 8, 9, 10, 11 or 12) nucleotides selected from the group consisting of $k_{12}$, $c_{13}$, $a_{14}$, $c_{15}$, $n_{16}$, $n_{17}$, $n_{18}$, $g_{19}$, $a_{20}$, $g_{21}$, $a_{22}$ and $t_{23}$. In certain embodiments, oligonucleotide decoys comprising a deletion of one or more nucleotides selected from the group consisting of $k_{12}$, $c_{13}$, $a_{14}$, $c_{15}$, $n_{16}$, $n_{17}$, $n_{18}$, $g_{19}$, $a_{20}$, $g_{21}$, $a_{22}$ and $t_{23}$ have at least 60% identity to the nucleotide sequence of SEQ ID NO.: 21.

In certain embodiments, an oligonucleotide decoy comprises a double-stranded sequence represented by formula (22):

(22) 5' - $S_1n_2n_3n_4n_5K_6C_7M_8T_9W_{10}A_{11}W_{12}t_{13}r_{14}m_{15}W_{16}n_{17}r_{18}m_{19}w_{20}$ . . .

. . . $K_{21}C_{22}M_{23}T_{24}W_{25}A_{26}W_{27}T_{28}n_{29}n_{30}n_{31}S_{32}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can an A or a T, "K" can be a G or a T, "M" can be an A or a C, "R" can be an A or a G, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (22) has at least about 65%, 70%, 75%, 80%, 85%, 90%, 91%, 92%, 93%, 94%, 95%, 96%, 97%, 98%, or 99% sequence identity to the nucleotide sequence of SEQ ID NO.: 22. Such oligonucleotide decoys can bind to POU4F1 transcription factor. In certain embodiments, such oligonucleotide decoys can bind to one or more transcription factors closely related to POU4F1 transcription factor, such as POU4F2-3.

In certain embodiments, an oligonucleotide decoy represented by formula (22) comprises a deletion of one or more (e.g., 1, 2, 3, 4, 5, 6, 7 or 8) nucleotides selected from the group consisting of $t_{13}$, $r_{14}$, $m_{15}$, $w_{16}$, $n_{17}$, $r_{18}$, $m_{19}$ and $w_{20}$. In certain embodiments, oligonucleotide decoys comprising a deletion of one or more nucleotides selected from the group consisting of $t_{13}$, $r_{14}$, $m_{15}$, $w_{16}$, $n_{17}$, $r_{18}$, $m_{19}$ and $w_{20}$ have at least 65% identity to the nucleotide sequence of SEQ ID NO.: 22.

In certain embodiments, an oligonucleotide decoy comprises a double-stranded sequence represented by formula (23):

(23) 5' - $S_1n_2n_3n_4A_5G_6K_7A_8A_9A_{10}D_{11}N_{12}D_{13}T_{14}h_{15}h_{16}h_{17}n_{18}n_{19}n_{20}$ . . .

. . . $h_{21}h_{22}H_{23}Y_{24}A_{25}A_{26}D_{27}N_{28}D_{29}T_{30}W_{31}V_{32}M_{33}t_{34}g_{35}c_{36}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "V" can be G, A or C, "K" can be T or G, "D" can be G, A or T, "H" can be A, T or C, "W" can be A or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (23) has at least about 55%, 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 23. Such oligonucleotide decoys can bind to HNF1A transcription factor. In certain embodiments, such oligonucleotide decoys can bind to one or more transcription factors closely related to HNF1A transcription factor, such as HNF1B-C.

In certain embodiments, an oligonucleotide decoy represented by formula (23) comprises a deletion of one or more (e.g., 1, 2, 3, 4, 5, 6, 7 or 8) nucleotides selected from the group consisting of $h_{15}$, $h_{16}$, $h_{17}$, $n_{18}$, $n_{19}$, $n_{20}$, $h_{21}$ and $h_{22}$. In certain embodiments, oligonucleotide decoys comprising a deletion of one or more nucleotides selected from the group consisting of $h_{15}$, $h_{16}$, $h_{17}$, $n_{18}$, $n_{19}$, $n_{20}$, $h_{21}$ and $h_{22}$ have at least 55% identity to the nucleotide sequence of SEQ ID NO.: 23.

In certain embodiments, an oligonucleotide decoy comprises a double-stranded sequence represented by formula (24):

(24) 5' - $S_1n_2n_3n_4n_5A_6A_7T_8A_9A_{10}t_{11}n_{12}n_{13}a_{14}t_{15}T_{16}A_{17}T_{18}T_{19}w_{20}$ . . .

. . . $w_{21}n_{22}n_{23}n_{24}S_{25}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (24) has at least about 80%, 85%, 90%, 91%, 92%, 93%, 94%, 95%, 96%, 97%, 98%, or 99% sequence identity to the nucleotide sequence of SEQ ID NO.: 24. Such oligonucleotide decoys can bind to ZFHX3 transcription factor. In certain embodiments, such oligonucleotide decoys can bind to one or more transcription factors closely related to ZFHX3 transcription factor, such as ZFHX-2, -4.

In certain embodiments, an oligonucleotide decoy represented by formula (24) comprises a deletion of one or more (e.g., 1, 2, 3, 4 or 5) nucleotides selected from the group consisting of $t_{11}$, $n_{12}$, $n_{13}$, $a_{14}$ and $t_{15}$. In certain embodiments, oligonucleotide decoys comprising a deletion of one or more nucleotides selected from the group consisting of $t_{11}$, $n_{12}$, $n_{13}$, $a_{14}$ and $t_{15}$ have at least 80% identity to the nucleotide sequence of SEQ ID NO.: 24.

In certain embodiments, an oligonucleotide decoy comprises a double-stranded sequence represented by formula (25):

(25) 5' - $S_1n_2n_3n_4S_5D_6H_7W_8M_9S_{10}H_{11}k_{12}w_{13}w_{14}m_{15}c_{16}s_{17}s_{18}d_{19}h_{20}$ . . .

. . . $w_{21}m_{22}s_{23}h_{24}K_{25}W_{26}W_{27}M_{28}C_{29}S_{30}n_{31}n_{32}n_{33}n_{34}S_{35}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or T, "D" can be A, G or T, "H" can be A, C or T, "M" can be A or C, "K" can be G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (25) has at least about 80%, 85%, 90%, 91%, 92%, 93%, 94%, 95%, 96%, 97%, 98%, or 99% sequence identity to the nucleotide sequence of SEQ ID NO.: 25. Such oligonucleotide decoys can bind to IRF1 transcription factor. In certain embodiments, such oligonucleotide decoys can bind to one or more transcription factors closely related to IRF1 transcription factor, such as IRF2.

In certain embodiments, an oligonucleotide decoy represented by formula (25) comprises a deletion of one or more (e.g., 1, 2, 3, 4, 5, 6, 7, 8, 9, 10, 11, 12 or 13) nucleotides selected from the group consisting of $k_{12}$, $w_{13}$, $w_{14}$, $m_{15}$, $c_{16}$, $s_{17}$, $s_{18}$, $d_{19}$, $h_{20}$, $w_{21}$, $m_{22}$, $s_{23}$ and $h_{24}$. In certain embodiments, oligonucleotide decoys comprising a deletion of one or more nucleotides selected from the group consisting of $k_{12}$, $w_{13}$, $w_{14}$, $m_{15}$, $c_{16}$, $s_{17}$, $s_{18}$, $d_{19}$, $h_{20}$, $w_{21}$, $m_{22}$, $s_{23}$ and $h_{24}$ have at least 80% identity to the nucleotide sequence of SEQ ID NO.: 25.

In certain embodiments, an oligonucleotide decoy comprises a double-stranded sequence represented by formula (26):

(26) 5' - $S_1n_2n_3n_4Y_5k_6g_7Y_8k_9G_{10}A_{11}A_{12}Y_{13}h_{14}b_{15}b_{16}n_{17}n_{18}n_{19}Y_{20}$ . . .

. . . $h_{21}b_{22}b_{23}k_{24}G_{25}A_{26}A_{27}T_{28}A_{29}T_{30}C_{31}n_{32}n_{33}S_{34}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "V" can be G, A or C, "K" can be T or G, "D" can be G, A or T, "H" can be A, T or G, "B" can be C, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (26) has at least about 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 26. Such oligonucleotide decoys can bind to TEAD1 transcription factor. In certain embodiments, such oligonucleotide decoys can bind to one or more transcription factors closely related to TEAD1 transcription factor, such as TEAD2-4.

In certain embodiments, an oligonucleotide decoy represented by formula (26) comprises a deletion of one or more (e.g., 1, 2, 3, 4, 5, 6, 7, 8, 9, 10, 11 or 12) nucleotides selected from the group consisting of $y_{13}$, $h_{14}$, $b_{15}$, $b_{16}$, $n_{17}$, $n_{18}$, $n_{19}$, $y_{20}$, $h_{21}$, $h_{22}$, $b_{23}$ and $k_{24}$. In certain embodiments, oligonucleotide decoys comprising a deletion of one or more nucleotides selected from the group consisting of $y_{13}$, $h_{14}$, $b_{15}$, $b_{16}$, $n_{17}$, $n_{18}$, $n_{19}$, $y_{20}$, $h_{21}$, $b_{22}$, $b_{23}$ and $k_{24}$ have at least 60% identity to the nucleotide sequence of SEQ ID NO.: 26.

In certain embodiments, an oligonucleotide decoy comprises a double-stranded sequence represented by formula (27):

(27) 5' - $S_1n_2n_3n_4T_5A_6T_7A_8W_9w_{10}w_{11}n_{12}n_{13}d_{14}n_{15}t_{16}a_{17}t_{18}A_{19}W_{20}$ . . .

. . . $w_{21}w_{22}n_{23}n_{24}w_{25}W_{26}T_{27}A_{28}A_{29}D_{30}W_{31}n_{32}n_{33}n_{34}n_{35}n_{36}S_{37}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or a T, "D" can be an A, G or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (27) has at least about 75%, 80%, 85%, 90%, 91%, 92%, 93%, 94%, 95%, 96%, 97%, 98%, or 99% sequence identity to the nucleotide sequence of SEQ ID NO.: 27. Such oligonucleotide decoys can bind to TBP transcription factor. In certain embodiments, such oligonucleotide decoys can bind to one or more transcription factors closely related to TBP transcription factor, such as TBPL1-2.

In certain embodiments, an oligonucleotide decoy represented by formula (27) comprises a deletion of one or more (e.g., 1, 2, 3, 4, 5, 6, 7, 8, 9, 10, 11, 12, 13 or 14) nucleotides selected from the group consisting of $w_{10}$, $w_{11}$, $n_{12}$, $n_{13}$, $d_{14}$, $n_{15}$, $t_{16}$, $a_{17}$, $t_{18}$, $w_{21}$, $w_{22}$, $n_{23}$, $n_{24}$, and $w_{25}$. In certain embodiments, oligonucleotide decoys comprising a deletion of one or more nucleotides selected from the group consisting of $w_{10}$, $w_{11}$, $n_{12}$, $n_{13}$, $d_{14}$, $n_{15}$, $t_{16}$, $a_{17}$, $t_{18}$, $w_{21}$, $w_{22}$, $n_{23}$, $n_{24}$, and $w_{25}$ have at least 75% identity to the nucleotide sequence of SEQ ID NO.: 27.

In certain embodiments, an oligonucleotide decoy comprises a double-stranded sequence represented by formula (28):

(28) 5' - $S_1n_2n_3n_4T_5A_6T_7A_8A_9W_{10}W_{11}n_{12}n_{13}n_{14}n_{15}W_{16}W_{17}W_{18}A_{19}A_{20}$ . . .

. . . $W_{21}W_{22}k_{23}n_{24}n_{25}n_{26}n_{27}n_{28}S_{29}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or a T, "K" can be a G or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (28) has at least about 65%, 70%, 75%, 80%, 85%, 90%, 91%, 92%, 93%, 94%, 95%, 96%, 97%, 98%, or 99% sequence identity to the nucleotide sequence of SEQ ID NO.: 28. Such oligonucleotide decoys can bind to TBP transcription factors. In certain embodiments, such oligonucleotide decoys can bind to one or more transcription factors closely related to TBP transcription factors, such as TBPL1-2.

In certain embodiments, an oligonucleotide decoy represented by formula (28) comprises a deletion of one or more (e.g., 1, 2, 3, 4, 5, 6 or 7) nucleotides selected from the group consisting of $n_{12}$, $n_{13}$, $n_{14}$, $n_{15}$, $w_{16}$, $w_{17}$ and $w_{18}$. In certain embodiments, oligonucleotide decoys comprising a deletion of one or more nucleotides selected from the group consisting of $n_{12}$, $n_{13}$, $n_{14}$, $n_{15}$, $w_{16}$, $w_{17}$ and $w_{18}$ have at least 65% identity to the nucleotide sequence of SEQ ID NO.: 28.

In certain embodiments, an oligonucleotide decoy comprises a double-stranded sequence represented by formula (29):

$$(29)\ 5'\ -\ N_1n_2n_3C_4T_5G_6M_7K_8Y_9K_{10}K_{11}Y_{12}t_{13}m_{14}b_{15}Y_{16}C_{17}A_{18}A_{19}T_{20}\ \ldots$$
$$\ldots\ s_{21}d_{22}n_{23}n_{24}n_{25}S_{26}\ -\ 3'$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "M" can be an A or a C, "K" can be a G or a T, "Y" can be a C or a T, "B" can be a C, G or T, "D" can be an A, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (29) has at least about 75%, 80%, 85%, 90%, 91%, 92%, 93%, 94%, 95%, 96%, 97%, 98%, or 99% sequence identity to the nucleotide sequence of SEQ ID NO.: 29. Such oligonucleotide decoys can bind to NFYA transcription factor. In certain embodiments, such oligonucleotide decoys can bind to one or more transcription factors closely related to NFYA transcription factor, such as NFYB-C.

In certain embodiments, an oligonucleotide decoy represented by formula (29) comprises a deletion of one or more (e.g., 1, 2, 3 or 4) nucleotides selected from the group consisting of $t_{13}$, $m_{14}$, $b_{15}$ and $y_{16}$. In certain embodiments, oligonucleotide decoys comprising a deletion of one or more nucleotides selected from the group consisting of $t_{13}$, $m_{14}$, $b_{15}$ and $y_{16}$ have at least 75% identity to the nucleotide sequence of SEQ ID NO.: 29.

In certain embodiments, an oligonucleotide decoy comprises a double-stranded sequence represented by formula (30):

$$(30)\ 5'\ -\ S_1n_2n_3T_4C_5T_6C_7Y_8G_9A_{10}T_{11}T_{12}G_{13}G_{14}Y_{15}Y_{16}h_{17}Y_{18}b_{19}n_{20}\ \ldots$$
$$\ldots\ n_{21}n_{22}Y_{23}Y_{24}h_{25}h_{26}v_{27}G_{28}A_{29}T_{30}T_{31}G_{32}G_{33}Y_{34}T_{35}C_{36}B_{37}Y_{38}n_{39}S_{40}\ -\ 3'$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "H" can be A, T or C, "B" can be C, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (30) has at least about 50%, 55%, 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 30. Such oligonucleotide decoys can bind to NFYA transcription factor. In certain embodiments, such oligonucleotide decoys can bind to one or more transcription factors closely related to NFYA transcription factor, such as NFYB-C.

In certain embodiments, an oligonucleotide decoy represented by formula (30) comprises a deletion of one or more (e.g., 1, 2, 3, 4, 5, 6, 7, 8, 9, 10, 11 or 12) nucleotides selected from the group consisting of $y_{16}$, $h_{17}$, $y_{18}$, $b_{19}$, $n_{20}$, $n_{21}$, $n_{22}$, $y_{23}$, $y_{24}$, $h_{25}$, $h_{26}$ and $v_{27}$. In certain embodiments, oligonucleotide decoys comprising a deletion of one or more nucleotides selected from the group consisting of $y_{16}$, $h_{17}$, $y_{18}$, $b_{19}$, $n_{20}$, $n_{21}$, $n_{22}$, $y_{23}$, $y_{24}$, $h_{25}$, $h_{26}$ and $v_{27}$ have at least 50% identity to the nucleotide sequence of SEQ ID NO.: 30.

In certain embodiments, an oligonucleotide decoy comprises a double-stranded sequence represented by formula (31):

$$(31)\ 5'\ -\ S_1n_2n_3C_4A_5C_6C_7C_8s_9a_{10}s_{11}s_{12}s_{13}w_{14}s_{15}s_{16}s_{17}w_{18}C_{19}A_{20}\ \ldots$$
$$\ldots\ C_{21}C_{22}C_{23}a_{24}n_{25}n_{26}n_{27}S_{28}\ -\ 3'$$

wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or a T, lower case letters can optionally be deleted, and the numbers in subscript represent the position of a nucleotide in the sequence. Although the formula shows a single strand, it should be understood that a complementary strand is included as part of the structure.

In preferred embodiments, an oligonucleotide decoy having a sequence represented by formula (31) has at least about 75%, 80%, 85%, 90%, 91%, 92%, 93%, 94%, 95%, 96%, 97%, 98%, or 99% sequence identity to the nucleotide sequence of SEQ ID NO.: 31. Such oligonucleotide decoys can bind to CACCC-box binding factors.

In certain embodiments, an oligonucleotide decoy represented by formula (31) comprises a deletion of one or more (e.g., 1, 2, 3, 4, 5, 6, 7, 8, 9 or 10) nucleotides selected from the group consisting of $s_9$, $a_{10}$, $s_{11}$, $s_{12}$, $d_{13}$, $w_{14}$, $s_{15}$, $d_{16}$, $s_{17}$ and $w_{18}$. In certain embodiments, oligonucleotide decoys comprising a deletion of one or more nucleotides selected from the group consisting of $s_9$, $a_{10}$, $s_{11}$, $s_{12}$, $s_{13}$, $w_{14}$, $s_{15}$, $s_{16}$, $s_{17}$ and $w_{18}$ have at least 75% identity to the nucleotide sequence of SEQ ID NO.: 31.

In certain embodiments, an oligonucleotide decoy comprises a double-stranded sequence represented by formula (32):

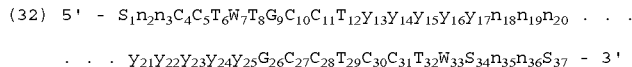

(32) 5' - $S_1n_2n_3C_4C_5T_6W_7T_8G_9C_{10}C_{11}T_{12}y_{13}y_{14}y_{15}y_{16}y_{17}n_{18}n_{19}n_{20}$ . . .
. . . $y_{21}y_{22}y_{23}y_{24}y_{25}G_{26}C_{27}C_{28}T_{29}C_{30}C_{31}T_{32}W_{33}S_{34}n_{35}n_{36}S_{37}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "W" can be A or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (32) has at least about 50%, 55%, 60%, 65%70%, 75%, 80%, 85%, 88%, 90%, 91%, 92%, 93%, 94%, 95%, 96%, 97%, 98%, or 99% sequence identity to the nucleotide sequence of SEQ ID NO.: 32. Such oligonucleotide decoys can bind to KLF4 transcription factor. In certain embodiments, such oligonucleotide decoys can bind to one or more transcription factors closely related to KLF4 transcription factor, such as KLF-1, -5.

In certain embodiments, an oligonucleotide decoy represented by formula (32) comprises a deletion of one or more (e.g., 1, 2, 3, 4, 5, 6, 7, 8, 9, 10, 11, 12 or 13) nucleotides selected from the group consisting of $y_{13}$, $y_{14}$, $y_{15}$, $y_{16}$, $y_{17}$, $n_{18}$, $n_{19}$, $n_{20}$, $y_{21}$, $y_{22}$, $y_{23}$, $y_{24}$ and $y_{25}$. In certain embodiments, oligonucleotide decoys comprising a deletion of one or more nucleotides selected from the group consisting of $y_{13}$, $y_{14}$, $y_{15}$, $y_{16}$, $y_{17}$, $n_{18}$, $n_{19}$, $n_{20}$, $y_{21}$, $y_{22}$, $y_{23}$, $y_{24}$ and $y_{25}$ have at least 50% identity to the nucleotide sequence of SEQ ID NO.: 32.

In certain embodiments, an oligonucleotide decoy comprises a double-stranded sequence represented by formula (33):

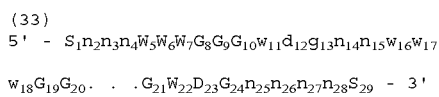

(33) 5' - $S_1n_2n_3n_4W_5W_6W_7G_8G_9G_{10}w_{11}d_{12}g_{13}n_{14}n_{15}w_{16}w_{17}$
$w_{18}G_{19}G_{20}$. . . $G_{21}W_{22}D_{23}G_{24}n_{25}n_{26}n_{27}n_{28}S_{29}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or a T, "D" can be an A, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (33) has at least about 75%, 80%, 85%, 90%, 91%, 92%, 93%, 94%, 95%, 96%, 97%, 98%, or 99% sequence identity to the nucleotide sequence of SEQ ID NO.: 33. Such oligonucleotide decoys can bind to KLF7 transcription factor. In certain embodiments, such oligonucleotide decoys can bind to one or more transcription factors closely related to KLF7 transcription factor, such as KLF-1, -2, and -5.

In certain embodiments, an oligonucleotide decoy represented by formula (33) comprises a deletion of one or more (e.g., 1, 2, 3, 4, 5, 6, 7 or 8) nucleotides selected from the group consisting of $w_{11}$, $d_{12}$, $g_{13}$, $n_{14}$, $n_{15}$, $w_{16}$, $w_{17}$ and $w_{18}$. In certain embodiments, oligonucleotide decoys comprising a deletion of one or more nucleotides selected from the group consisting of $w_{11}$, $d_{12}$, $g_{13}$, $n_{14}$, $n_{15}$, $w_{16}$, $w_{17}$ and $w_{18}$ have at least 75% identity to the nucleotide sequence of SEQ ID NO.: 33.

In certain embodiments, an oligonucleotide decoy comprises a double-stranded sequence represented by formula (34):

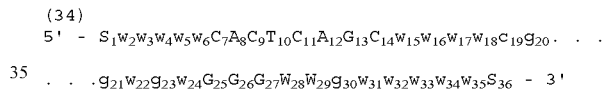

(34)
5' - $S_1W_2W_3W_4W_5W_6C_7A_8C_9T_{10}C_{11}A_{12}G_{13}C_{14}W_{15}W_{16}W_{17}W_{18}C_{19}g_{20}$. . .
. . . $g_{21}W_{22}g_{23}W_{24}G_{25}G_{26}G_{27}W_{28}W_{29}g_{30}W_{31}W_{32}W_{33}W_{34}W_{35}S_{36}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (34) has at least about 55%, 60%, 65%, 70%, 75%, 80%, 85%, 90%, 91%, 92%, 93%, 94%, 95%, 96%, 97%, 98%, or 99% sequence identity to the nucleotide sequence of SEQ ID NO.: 34. Such oligonucleotide decoys can bind to MAFG transcription factor. In certain embodiments, such oligonucleotide decoys can bind to one or more transcription factors closely related to MAFG transcription factor, such as MAF-A, -B, -F, -K.

In certain embodiments, an oligonucleotide decoy represented by formula (34) comprises a deletion of one or more (e.g., 1, 2, 3, 4, 5, 6, 7, 8, 9 or 10) nucleotides selected from the group consisting of $w_{15}$, $w_{16}$, $w_{17}$, $w_{18}$, $c_{19}$, $g_{20}$, $g_{21}$, $w_{22}$, $g_{23}$ and $w_{24}$. In certain embodiments, oligonucleotide decoys comprising a deletion of one or more nucleotides selected from the group consisting of $w_{15}$, $w_{16}$, $w_{17}$, $w_{18}$, $c_{19}$, $g_{20}$, $g_{21}$, $w_{22}$, $g_{23}$ and $w_{24}$ have at least 55% identity to the nucleotide sequence of SEQ ID NO.: 34.

In certain embodiments, an oligonucleotide decoy comprises a double-stranded sequence represented by formula (35):

(35)
5' - $S_1n_2n_3W_4B_5Y_6A_7G_8Y_9A_{10}C_{11}C_{12}D_{13}N_{14}R_{15}G_{16}H_{17}$ $S_{18}A_{19}G_{20}\ldots C_{21}N_{22}N_{23}H_{24}n_{25}n_{26}n_{27}W_{28}B_{29}Y_{30}A_{31}G_{32}Y_{33}A_{34}C_{35}$ $C_{36}D_{37}N_{38}R_{39}G_{40}\ldots H_{41}S_{42}A_{43}G_{44}C_{45}N_{46}N_{47}H_{48}n_{49}n_{50}S_{51}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or a T, Y can be a C or a T, "H" can be an A, T or a C, "R" can be G or A, "D" can be G, A or T, "Y" can be C or T, "B" can be C, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (35) has at least about 50%, 55%, 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 35. Such oligonucleotide decoys can bind to REST transcription factor.

In certain embodiments, an oligonucleotide decoy represented by formula (35) comprises a deletion of one or more (e.g., 1, 2 or 3) nucleotides selected from the group consisting of $n_{25}$, $n_{26}$ and $n_{27}$. In certain embodiments, oligonucleotide decoys comprising a deletion of one or more nucleotides selected from the group consisting of $n_{25}$, $n_{26}$ and $n_{27}$ have at least 50% identity to the nucleotide sequence of SEQ ID NO.: 35.

In certain embodiments, an oligonucleotide decoy comprises a double-stranded sequence represented by formula (36):

(36)
5' - $S_1n_2n_3n_4n_5G_6A_7R_8M_9A_{10}W_{11}k_{12}s_{13}a_{14}g_{15}k_{16}n_{17}n_{18}n_{19}n_{20}\ldots$ $\ldots g_{21}a_{22}r_{23}m_{24}A_{25}W_{26}K_{27}S_{28}A_{29}G_{30}K_{31}n_{32}n_{33}n_{34}n_{35}S_{36}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or a T, "M" can be A or C, "R" can be A or G, "K" can be G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (36) has at least about 60%, 65%, 70%, 75%, 80%, 85%, 90%, 91%, 92%, 93%, 94%, 95%, 96%, 97%, 98%, or 99% sequence identity to the nucleotide sequence of SEQ ID NO.: 36. Such oligonucleotide decoys can bind to KCNIP3 transcription factor.

In certain embodiments, an oligonucleotide decoy represented by formula (36) comprises a deletion of one or more (e.g., 1, 2, 3, 4, 5, 6, 7, 8, 9, 10, 11, 12 or 13) nucleotides selected from the group consisting of $k_{12}$, $s_{13}$, $a_{14}$, $g_{15}$, $k_{16}$, $n_{17}$, $n_{18}$, $n_{19}$, $n_{20}$, $g_{21}$, $a_{22}$, $r_{23}$ and $m_{24}$. In certain embodiments, oligonucleotide decoys comprising a deletion of one or more nucleotides selected from the group consisting of $k_{12}$, $s_{13}$, $a_{14}$, $g_{15}$, $k_{16}$, $n_{17}$, $n_{18}$, $n_{19}$, $n_{20}$, $g_{21}$, $a_{22}$, $r_{23}$ and $m_{24}$ have at least 60% identity to the nucleotide sequence of SEQ ID NO.: 36.

In certain embodiments, an oligonucleotide decoy comprises a double-stranded sequence represented by formula (37):

(37)
5' - $S_1n_2n_3n_4n_5G_6A_7R_8G_9C_{10}C_{11}S_{12}S_{13}W_{14}g_{15}W_{16}n_{17}n_{18}n_{19}n_{20}\ldots$ $\ldots g_{21}a_{22}r_{23}G_{24}C_{25}C_{26}S_{27}S_{28}W_{29}G_{30}W_{31}n_{32}n_{33}n_{34}S_{35}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or a T, "M" can be A or C, "R" can be A or G, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (37) has at least about 75%, 80%, 85%, 90%, 91%, 92%, 93%, 94%, 95%, 96%, 97%, 98%, or 99% sequence identity to the nucleotide sequence of SEQ ID NO.: 37. Such oligonucleotide decoys can bind to KCNIP3 transcription factor.

In certain embodiments, an oligonucleotide decoy represented by formula (37) comprises a deletion of one or more (e.g., 1, 2, 3, 4, 5, 6, 7, 8, 9, 10 or 11) nucleotides selected from the group consisting of $s_{13}$, $w_{14}$, $g_{15}$, $w_{16}$, $n_{17}$, $n_{18}$, $n_{19}$, $n_{20}$, $g_{21}$, $a_{22}$ and $r_{23}$. In certain embodiments, oligonucleotide decoys comprising a deletion of one or more nucleotides selected from the group consisting of $s_{13}$, $w_{14}$, $g_{15}$, $w_{16}$, $n_{17}$, $n_{18}$, $n_{19}$, $n_{20}$, $g_{21}$, $a_{22}$ and $r_{23}$ have at least 75% identity to the nucleotide sequence of SEQ ID NO.: 37.

In certain embodiments, an oligonucleotide decoy comprises a double-stranded sequence represented by formula (38):

(38)
5' - $s_1C_2G_3A_4A_5A_6G_7G_8A_9C_{10}A_{11}A_{12}A_{13}s_{14}s_{15}n_{16}V_{17}V_{18}n_{19}n_{20}\ldots$ $\ldots n_{21}s_{22}g_{23}d_{24}n_{25}n_{26}G_{27}G_{28}A_{29}C_{30}A_{31}A_{32}A_{33}G_{34}G_{35}T_{36}C_{37}A_{38}$ $S_{39}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "V" can be A, C or G, "D" can be G, A or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (38) has at least about 50%, 55%, 60%, 65%, 70%, 75%, 80%, 85%, 88%, 90%, 91%, 92%, 93%, 94%, 95%, 96%, 97%, 98%, or 99% sequence identity to the nucleotide sequence of SEQ ID NO.: 38. Such oligonucleotide decoys can bind to PPARA transcription factor. In certain embodiments, such oligonucleotide decoys can bind to one or more transcription factors closely related to PPARA transcription factor, such as PPAR-D, -G.

In certain embodiments, an oligonucleotide decoy represented by formula (38) comprises a deletion of one or more (e.g., 1, 2, 3, 4, 5, 6, 7, 8, 9 or 10) nucleotides selected from the group consisting of $s_{14}$, $s_{15}$, $n_{16}$, $v_{17}$, $v_{18}$, $n_{19}$, $n_{20}$, $n_{21}$, $s_{22}$ and $g_{23}$. In certain embodiments, oligonucleotide decoys comprising a deletion of one or more nucleotides selected from the group consisting of $s_{14}$, $s_{15}$, $n_{16}$, $v_{17}$, $n_{18}$, $n_{19}$, $n_{20}$, $n_{21}$, $s_{22}$ and $g_{23}$ have at least 50% identity to the nucleotide sequence of SEQ ID NO.: 38.

In certain embodiments, an oligonucleotide decoy comprises a double-stranded sequence represented by formula (39):

(39)
5' - $S_1n_2n_3n_4A_5R_6M_7R_8W_9W_{10}Y_{11}W_{12}m_{13}g_{14}n_{15}n_{16}a_{17}r_{18}m_{19}r_{20}$...

...$W_{21}W_{22}Y_{23}W_{24}M_{25}G_{26}A_{27}A_{28}T_{29}T_{30}n_{31}n_{32}n_{33}n_{34}S_{35}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or a T, "R" can be A or G, "M" can be an A or a C, "Y" can be a C or a T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (39) has at least about 55%, 60%, 65%, 70%, 75%, 80%, 85%, 90%, 91%, 92%, 93%, 94%, 95%, 96%, 97%, 98%, or 99% sequence identity to the nucleotide sequence of SEQ ID NO.: 39. Such oligonucleotide decoys can bind to HSF1 transcription factor. In certain embodiments, the oligonucleotide decoys can bind to one or more transcription factors closely related to HSF1 transcription factor, such as HSF2.

In certain embodiments, an oligonucleotide decoy represented by formula (39) comprises a deletion of one or more (e.g., 1, 2, 3, 4, 5, 6, 7, 8, 9, 10, 11, 12 or 13) nucleotides selected from the group consisting of $y_{11}$, $w_{12}$, $m_{13}$, $g_{14}$, $n_{15}$, $n_{16}$, $a_{17}$, $r_{18}$, $m_{19}$, $r_{20}$, $w_{21}$, $w_{22}$ and $y_{23}$. In certain embodiments, oligonucleotide decoys comprising a deletion of one or more nucleotides selected from the group consisting of $y_{11}$, $w_{12}$, $m_{13}$, $g_{14}$, $n_{15}$, $n_{16}$, $a_{17}$, $r_{18}$, $m_{19}$, $r_{20}$, $w_{21}$, $w_{22}$ and $y_{23}$ have at least 55% identity to the nucleotide sequence of SEQ ID NO.: 39.

In certain embodiments, an oligonucleotide decoy comprises a double-stranded sequence represented by formula (47):

(47)
5' - $S_1n_2n_3n_4n_5n_6C_7A_8C_9T_{10}T_{11}C_{12}C_{13}T_{14}G_{15}C_{16}n_{17}n_{18}n_{19}n_{20}$ $n_{21}S_{22}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (47) has at least about 80%, 85%, 88%, 90%, 91%, 92%, 93%, 94%, 95%, 96%, 97%, 98%, or 99% sequence identity to the nucleotide sequence of SEQ ID NO.: 47. Such oligonucleotide decoys can bind to ELK1 transcription factor. In certain embodiments, such oligonucleotide decoys can bind to one or more transcription factors closely related to ELK1 transcription factor, such as ETS1.

In certain embodiments, an oligonucleotide decoy represented by formula (47) comprises a deletion of one or more (e.g., 1, 2, 3, 4, 5, 6, 7, 8, 9 or 10) nucleotides selected from the group consisting of $n_2$, $n_3$, $n_4$, $n_5$, $n_6$, $n_{17}$, $n_{18}$, $n_{19}$, $n_{20}$ and $n_{21}$. In certain embodiments, oligonucleotide decoys comprising a deletion of one or more nucleotides selected from the group consisting of $n_2$, $n_3$, $n_4$, $n_5$, $n_6$, $n_{17}$, $n_{18}$, $n_{19}$, $n_{20}$ and $n_{21}$ have at least 80% identity to the nucleotide sequence of SEQ ID NO.: 47.

In certain embodiments, an oligonucleotide decoy comprises a double-stranded sequence represented by formula (48):

(48)
5' - $S_1n_2n_3n_4n_5n_6A_7G_8K_9Y_{10}A_{11}A_{12}D_{13}N_{14}D_{15}T_{16}W_{17}V_{18}M_{19}N_{20}$...

...$n_{21}n_{22}n_{23}n_{24}n_{25}S_{26}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "V" can be G, A or C, "K" can be T or G, "D" can be G, A or T, "W" can be A or T, "M" can be C or A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (48) has at least about 70%, 75%, 80%, 85%, 88%, 90%, 91%, 92%, 93%, 94%, 95%, 96%, 97%, 98%, or 99% sequence identity to the nucleotide sequence of SEQ ID NO.: 48. Such oligonucleotide decoys can bind to HNF1A transcription factor. In certain embodiments, such oligonucleotide decoys can bind to one or more transcription factors closely related to HNF1A transcription factor, such as HNF1B-C.

In certain embodiments, an oligonucleotide decoy represented by formula (48) comprises a deletion of one or more (e.g., 1, 2, 3, 4, 5, 6, 7, 8, 9 or 10) nucleotides selected from the group consisting of $n_2$, $n_3$, $n_4$, $n_5$, $n_6$, $n_{21}$, $n_{22}$, $n_{23}$, $n_{24}$ and $n_{25}$. In certain embodiments, oligonucleotide decoys comprising a deletion of one or more nucleotides selected from the group consisting of $n_2$, $n_3$, $n_4$, $n_5$, $n_6$, $n_{21}$, $n_{22}$, $n_{23}$, $n_{24}$ and $n_{25}$ have at least 70% identity to the nucleotide sequence of SEQ ID NO.: 48.

In certain embodiments, an oligonucleotide decoy comprises a double-stranded sequence represented by formula (49):

(49)
5' - $S_1n_2n_3T_4C_5T_6C_7Y_8G_9A_{10}T_{11}T_{12}G_{13}G_{14}Y_{15}T_{16}C_{17}B_{18}Y_{19}$ $n_{20}S_{21}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "B" can be C, G or T, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (49) has at least about 80%, 85%, 88%, 90%, 91%, 92%, 93%, 94%, 95%, 96%, 97%, 98%, or 99% sequence identity to the nucleotide sequence of SEQ ID NO.: 49. Such oligonucleotide decoys can bind to NFYA transcription factor. In certain embodiments, such oligonucleotide decoys can bind to one or more transcription factors closely related to NFYA transcription factor, such as NFYB-C.

In certain embodiments, an oligonucleotide decoy represented by formula (49) comprises a deletion of one or more (e.g., 1, 2 or 3) nucleotides selected from the group consisting of $n_2$, $n_3$ and $n_{20}$. In certain embodiments, oligonucleotide decoys comprising a deletion of one or more nucleotides selected from the group consisting of $n_2$, $n_3$ and $n_{20}$ have at least 80% identity to the nucleotide sequence of SEQ ID NO.: 49.

In certain embodiments, an oligonucleotide decoy comprises a double-stranded sequence represented by formula (50):

(50)
5' - $S_1n_2n_3n_4n_5n_6C_7C_8T_9W_{10}T_{11}G_{12}C_{13}C_{14}T_{15}C_{16}C_{17}T_{18}W_{19}$

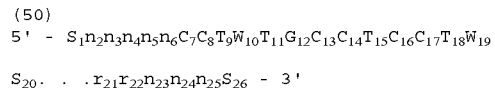

$S_{20}$... $r_{21}r_{22}n_{23}n_{24}n_{25}S_{26}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be A or T, "R" can be G or A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (50) has at least about 75%, 80%, 85%, 88%, 90%, 91%, 92%, 93%, 94%, 95%, 96%, 97%, 98%, or 99% sequence identity to the nucleotide sequence of SEQ ID NO.: 50. Such oligonucleotide decoys can bind to KLF4 transcription factor. In certain embodiments, such oligonucleotide decoys can bind to one or more transcription factors closely related to KLF4 transcription factor, such as KLF-1, -5.

In certain embodiments, an oligonucleotide decoy represented by formula (50) comprises a deletion of one or more (e.g., 1, 2, 3, 4, 5, 6, 7, 8, 9 or 10) nucleotides selected from the group consisting of $n_2$, $n_3$, $n_4$, $n_5$, $n_6$, $r_{21}$, $r_{22}$, $n_{23}$, $n_{24}$ and $n_{25}$. In certain embodiments, oligonucleotide decoys comprising a deletion of one or more nucleotides selected from the group consisting of $n_2$, $n_3$, $n_4$, $n_5$, $n_6$, $r_{21}$, $r_{22}$, $n_{23}$, $n_{24}$ and $n_{25}$ have at least 75% identity to the nucleotide sequence of SEQ ID NO.: 50.

In certain embodiments, an oligonucleotide decoy comprises a double-stranded sequence represented by formula (51):

(51)
5' - $S_1n_2n_3n_4n_5W_6B_7Y_8A_9G_{10}Y_{11}A_{12}C_{13}C_{14}D_{15}N_{16}R_{17}G_{18}$...

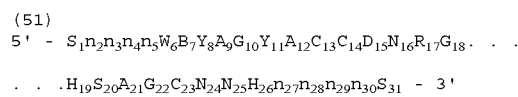

... $H_{19}S_{20}A_{21}G_{22}C_{23}N_{24}N_{25}H_{26}n_{27}n_{28}n_{29}n_{30}S_{31}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be an A or a T, "H" can be an A, T or a C, "R" can be G or A, "D" can be G, A or T, "Y" can be C or T, "B" can be C, G or T, lower case letters can optionally be deleted, and the numbers in subscript represent the position of a nucleotide in the sequence. Although the formula shows a single strand, it should be understood that a complementary strand is included as part of the structure.

In preferred embodiments, an oligonucleotide decoy having a sequence represented by formula (51) has at least about 75%, 80%, 85%, 88%, 90%, 91%, 92%, 93%, 94%, 95%, 96%, 97%, 98%, or 99% sequence identity to the nucleotide sequence of SEQ ID NO.: 51. Such oligonucleotide decoys can bind to REST transcription factor.

In certain embodiments, an oligonucleotide decoy represented by formula (51) comprises a deletion of one or more (e.g., 1, 2, 3, 4, 5, 6, 7 or 8) nucleotides selected from the group consisting of $n_2$, $n_3$, $n_4$, $n_5$, $n_{27}$, $n_{28}$, $n_{29}$ and $n_{30}$. In certain embodiments, oligonucleotide decoys comprising a deletion of one or more nucleotides selected from the group consisting of $n_2$, $n_3$, $n_4$, $n_5$, $n_{27}$, $n_{28}$, $n_{29}$ and $n_{30}$ have at least 75% identity to the nucleotide sequence of SEQ ID NO.: 51.

In certain embodiments, an oligonucleotide decoy comprises a double-stranded sequence represented by formula (52):

(52)
5' - $S_1m_2r_3m_4W_5A_6G_7G_8N_9C_{10}A_{11}A_{12}A_{13}G_{14}G_{15}T_{16}C_{17}A_{18}n_{19}$

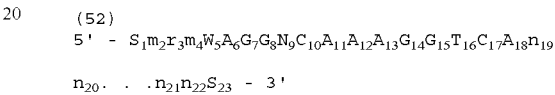

$n_{20}$... $n_{21}n_{22}S_{23}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "W" can be A or T, "R" can be G or A, "M" can be C or A, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (52) has at least about 80%, 85%, 88%, 90%, 91%, 92%, 93%, 94%, 95%, 96%, 97%, 98%, or 99% sequence identity to the nucleotide sequence of SEQ ID NO.: 52. Such oligonucleotide decoys can bind to PPARA transcription factor. In certain embodiments, such oligonucleotide decoys can bind to one or more transcription factors closely related to PPARA transcription factor, such as PPAR-D, -G.

In certain embodiments, an oligonucleotide decoy represented by formula (52) comprises a deletion of one or more (e.g., 1, 2, 3, 4, 5, 6, 7 or 8) nucleotides selected from the group consisting of $m_2$, $r_3$, $m_4$, $n_{19}$, $n_{20}$, $n_{21}$, $n_{22}$ and $g_{23}$. In certain embodiments, oligonucleotide decoys comprising a deletion of one or more nucleotides selected from the group consisting of $m_2$, $r_3$, $M_4$, $n_{19}$, $n_{20}$, $n_{21}$, $n_{22}$ and $g_{23h}$ have at least 80% identity to the nucleotide sequence of SEQ ID NO.: 52.

In certain embodiments, an oligonucleotide decoy comprises a double-stranded sequence represented by formula (53):

(53)
5' - $S_1S_2C_3t_4t_5g_6Y_7k_8g_9Y_{10}k_{11}G_{12}k_{13}A_{14}T_{15}A_{16}T_{17}C_{18}g_{19}$

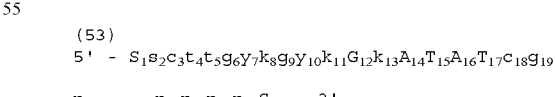

$n_{20}$... $n_{21}n_{22}n_{23}n_{24}S_{25}$ - 3' wherein "A" is an adenine nucleotide, "C" is a cytosine nucleotide, "G" is a guanine nucleotide, "T" is a thymine nucleotide, "S" can be a G or C nucleotide, "N" can be any nucleotide, "Y" can be T or C, "K" can be T or G, lower case letters can optionally be deleted, and the numbers in subscript represent the position of a nucleotide in the sequence. Although the formula shows a single strand, it should be understood that a complementary strand is included as part of the structure. In preferred embodiments, an oligonucleotide decoy having a sequence represented by formula (53) has at least about 75%, 80%, 85%, 88%, 90%, 91%, 92%, 93%, 94%, 95%, 96%, 97%, 98%, or 99% sequence identity to the nucleotide sequence of SEQ ID NO.: 53. Such oligonucleotide decoys can bind to TEAD1 transcription factor. In certain embodiments, such oligonucleotide decoys can bind to one or more transcription factors closely related to TEAD1 transcription factor, such as TEAD2-4.

In certain embodiments, an oligonucleotide decoy represented by formula (53) comprises a deletion of one or more (e.g., 1, 2, 3, 4, 5, 6, 7, 8, 9, 10, 11, 12, 13, 14, 15, 16 or 17) nucleotides selected from the group consisting of $s_2$, $c_3$, $t_4$, $t_5$, $g_6$, $y_7$, $k_8$, $g_9$, $y_{10}$, $k_{11}$, $c_{18}$, $g_{19}$, $n_{20}$, $n_{21}$, $n_{22}$, $n_{23}$ and $n_{24}$. In certain embodiments, oligonucleotide decoys comprising a deletion of one or more nucleotides selected from the group consisting of $s_2$, $c_3$, $t_4$, $t_5$, $g_6$, $y_7$, $k_8$, $g_9$, $y_{10}$, $k_{11}$, $c_{18}$, $g_{19}$, $n_{20}$, $n_{21}$, $n_{22}$, $n_{23}$ and $n_{24}$ have at least 75% identity to the nucleotide sequence of SEQ ID NO.: 53.

A double stranded oligonucleotide having a certain percent (e.g., 65%, 70%, 75%, 80%, 85%, 90%, 95%, or 99%) of sequence identity with another sequence means that, when aligned, that percentage determines the level of correspondence of bases arrangement in comparing the two sequences. This alignment and the percent homology or identity can be determined using any suitable software program known in the art that allows local alignment. The software program should be capable of finding regions of local identity between two sequences without the need to include the entire length of the sequences. In some embodiments, such program includes but is not limited to the EMBOSS Pairwise Alignment Algorithm (available from the European Bioinformatics Institute (EBI)), the ClustalW program (also available from the European Bioinformatics Institute (EBI)), or the BLAST program (BLAST Manual, Altschul et al., Natl Cent. Biotechnol. Inf., Natl Lib. Med. (NCIB NLM NIH), Bethesda, Md., and Altschul et al., (1997) NAR 25:3389 3402).

One skilled in the art will recognize that sequences encompassed herein include those that hybridize under stringent hybridization conditions with an exemplified sequence (e.g., SEQ ID NOs.: 1-42, 45, and 47-53). A nucleic acid is hybridizable to another nucleic acid when a single stranded form of the nucleic acid can anneal to the other single stranded nucleic acid under appropriate conditions of temperature and solution ionic strength. Hybridization conditions are well known in the art. In some embodiments, annealing can occur during a slow decrease of temperature from a denaturing temperature (e.g., 100° C.) to room temperature in a salt containing solvent (e.g., Tris-EDTA buffer).

The oligonucleotide decoys disclosed herein can be chemically modified by methods well known to the skilled artisan (e.g., incorporation of phosphorothioate, methylphosphonate, phosphorodithioate, phosphoramidates, carbonate, thioether, siloxane, acetamidate or carboxymethyl ester linkages between nucleotides) to prevent degradation by nucleases within cells and extra-cellular fluids (e.g., serum, cerebrospinal fluid). Also, oligonucleotide decoys can be designed that form hairpin and dumbbell structures which also prevent or hinder nuclease degradation. Further, the oligonucleotide decoys can also be inserted as a portion of a larger plasmid capable of episomal maintenance or constitutive replication in the target cell in order to provide longer term, enhanced intracellular exposure to the decoy sequence or reduce its degradation. Accordingly, any chemical modification or structural alteration known in the art to enhance oligonucleotide stability is within the scope of the present disclosure. In some embodiments, the oligonucleotide decoys disclosed herein can be attached, for example, to polyethylene glycol polymers, peptides (e.g., a protein translocation domain) or proteins which improve the therapeutic effect of oligonucleotide decoys. Such modified oligonucleotide decoys can preferentially traverse the cell membrane.

In certain embodiments, the oligonucleotide decoys are provided as salts, hydrates, solvates, or N-oxide derivatives. In certain embodiments, the oligonucleotide decoys are provided in solution (e.g., a saline solution having a physiologic pH) or in lyophilized form. In other embodiments, the oligonucleotide decoys are provided in liposomes.

In certain embodiments, oligonucleotide decoys include, but are not limited to, sequences presented in Table A. In general, the oligonucleotide decoy is generated by annealing the sequence provided in the table with a complementary sequence. To generate a mismatch double-stranded oligonucleotide, the sequence provided in the table can be annealed to a sequence that is only partially complementary. For example, SEQ ID NO.:43 can be annealed to SEQ ID NO.:46 to produce the mismatched sequence, SEQ ID NO.:43/46.

TABLE A

| Oligonucleotide Sequences (5'-3') | SEQ ID NO. |
|---|---|
| GGCTTATGCAAATTCGAATGCAAATTTGTCG | SEQ ID NO.: 1 |
| CTAAGCCCACGTGACCATTGGCCAGGTGACCAGATC | SEQ ID NO.: 2 |
| GTTATGCGTGGGCGATAATGCGGGGCGTTATAG | SEQ ID NO.: 3 |
| GCCTCCCTGAGCTCATTGACGTATCTCGG | SEQ ID NO.: 4 |
| CGAATATGACTGAGAATGACTCAGATTTGC | SEQ ID NO.: 5 |
| GGTTCTATGATTTTGGAATCGGATTGTGCAAAGAAGC | SEQ ID NO.: 6 |
| GCTTCAGGATGTCCATATTAGGAGATCTTGTTCG | SEQ ID NO.: 7 |
| GGCCACAGGATGTAGGATGTCCATATTAGGATGC | SEQ ID NO.: 8 |
| GTTCTCTAAAAATAAAAGGCTAAAAATAAAAGTCG | SEQ ID NO.: 9 |
| ATTAGGGGCGGGGTCCGGGGCGGGGTATTA | SEQ ID NO.: 10 |
| GTTATGGCGGGGCGGGGCGGGGCCGGGCGGTTTAC | SEQ ID NO.: 11 |
| GGCAATGTGGTTTTAGTGTGGTTTTACGG | SEQ ID NO.: 12 |
| GCCGTTTGGGGTCATAGAACCACAGGAACCACACGG | SEQ ID NO.: 13 |
| CATTGCCCGGAAATGGACCGGATGTAATTTCC | SEQ ID NO.: 14 |
| GTTCTTGGAAAATAAATGGAAAATAGTGGAAAATAAGTCG | SEQ ID NO.: 15 |
| CGTTCCCACTTCCTGCGACCACTTCCTGCCGGG | SEQ ID NO.: 16 |
| CTGCACCTATAAATGGCCTATAAATGGGGATGC | SEQ ID NO.: 17 |
| GCTTATTTCGCGGAAGGTTTCCCGGAAGTGGCG | SEQ ID NO.: 18 |
| GCTGTGCCTTATCTCTTTGGGATAACTGGCG | SEQ ID NO.: 19 |
| GCTTAATGAATAAGAGGAAAAATGCATGCTGG | SEQ ID NO.: 20 |
| GTTCTGAGATTGCACGATGAGATTTCACAGTCG | SEQ ID NO.: 21 |
| GTCCCGCATAAATAATGGCATCCTTAATCGCG | SEQ ID NO.: 22 |

TABLE A-continued

| Oligonucleotide Sequences (5'-3') | SEQ ID NO. |
|---|---|
| GTGCAGGCAAGAGTAGAGACAGGCAAGAGTAGATGC | SEQ ID NO.: 23 |
| CCGCCAATAATTAATTATTAAGGCC | SEQ ID NO.: 24 |
| GCTTCGTTCCATTTCCGGTCTCGGTTTCCCCATTC | SEQ ID NO.: 25 |
| GCTGCTGTGGAATATCGACCTGTGGAATATCGTG | SEQ ID NO.: 26 |
| GCCGTATAAATGTGCTATAAAAGTTTTAAGACCGTGC | SEQ ID NO.: 27 |
| GCCGTATAAATGTGCTATAAAAGCCGTGC | SEQ ID NO.: 28 |
| ATGCTGCGCTTTTCTCCAATCTGCGG | SEQ ID NO.: 29 |
| CGTTCTCCGATTGGTCACGGACTCTCCGATTGGTCACGGC | SEQ ID NO.: 30 |
| GCGCACCCCAGCCTGGCTCACCCACGCG | SEQ ID NO.: 31 |
| GATCCTTTGCCTCCTTCGATCCTTTGCCTCCTTCAAG | SEQ ID NO.: 32 |
| GGTGTTTGGGAGAGCTTTGGGAGGATACG | SEQ ID NO.: 33 |
| GCTAATCACTCAGCATTTCGGTGAGGGAAGTGAAAG | SEQ ID NO.: 34 |
| CCTTTCAGCACCACGGACAGCGCCAGCTTCAGCACCACGGACAGCGCCTCG | SEQ ID NO.: 35 |
| GGATCGAACATGGAGTCAGTGAGAAATCAGGATCGG | SEQ ID NO.: 36 |
| GGATCGAAGCCGGAGTCAAGGAGGCCCCTGATCGG | SEQ ID NO.: 37 |
| CCGAAAGGACAAAGGTCAAGTCGAAAGGACAAAGGTCAG | SEQ ID NO.: 38 |
| CGGGAGAAAATTCGGGAACGTTCAAGAATTGTCGG | SEQ ID NO.: 39 |
| GTTATGCGTGGGCGTAGATGCGGGGCGTTATAG | SEQ ID NO.: 40 |
| GATGCGTGGGCGTAGG | SEQ ID NO.: 41 |
| GTATGCGTGGGCGGTGGGCGTAG | SEQ ID NO.: 42 |
| GTTATGCGTTTGTAGATGCTTTCGTTATAG | SEQ ID NO.: 43 |
| GTTATGCGTGGGCGATATAG | SEQ ID NO.: 44 |
| GATGCGTGGGCGTTGACGTGGAAAATGC | SEQ ID NO.: 45 |
| CTATTTCGAAACGATCTACATTGGCATAAC | SEQ ID NO.: 46 |
| CGTTCCCACTTCCTGCGACCGG | SEQ ID NO.: 47 |
| GGGTGAAGGCAAGAGTAGAGCGGCGG | SEQ ID NO.: 48 |
| CGTTCTCCGATTGGTCACGCG | SEQ ID NO.: 49 |
| GTACTCCCTTTGCCTCCTTCAACCGG | SEQ ID NO.: 50 |
| CCTTATTCAGCACCACGGACAGCGCCATTCG | SEQ ID NO.: 51 |
| GCGAAAGGACAAAGGTCAGGCGG | SEQ ID NO.: 52 |
| GGCTTGCTGTGGAATATCGATGGTG | SEQ ID NO.: 53 |

According to the present invention, the composition of the present invention can further comprise a buffer. Any suitable buffer can be used for the composition of the present invention. In some embodiments, the buffer system used for the composition is compatible with the active ingredient and/or the agent in the composition. In some other embodiments, the buffer system used for the composition of the present invention facilitates or stabilizes the active ingredient and/or the agent. In some other embodiments, the buffer system used for the composition of the present invention is an organic or inorganic buffer. Examples of buffers include phosphate buffers, citrate buffers, borate buffers, bicarbonate buffers, carbonate buffers, acetate buffers, ammonium buffers, and tromethamine (Tris) buffers.

According to the present invention, in some embodiments, when the active ingredient is an oligonucleotide and the agent is an ion, e.g., calcium, the buffer is a non-phosphate based buffer. The amount of buffer employed will be ascertainable to a skilled artisan, such as an amount ranging from 0.01 mM to 1 M, such as 10 mM.

According to the present invention, the composition of the present invention can be a pharmaceutical composition, e.g., including a pharmaceutically acceptable carrier. Pharmaceutically acceptable carriers can contain a physiologically acceptable compound that acts, e.g., to stabilize the composition or to increase or decrease the absorption of the active ingredient and/or pharmaceutical composition. Physiologically acceptable compounds can include, for example, carbohydrates, such as glucose, sucrose, or dextrans, antioxidants, such as ascorbic acid or glutathione, chelating agents, low molecular weight proteins, compositions that reduce the clearance or hydrolysis of any co-administered agents, or excipient, or other stabilizers and/or buffers. Detergents can also be used to stabilize the composition or to increase or decrease absorption. One skilled in the art will appreciate that the choice of a pharmaceutically acceptable carrier, including a physiologically acceptable compound depends, e.g., on the route of administration of the present powders and on the particular physio-chemical characteristics of any co-administered agent.

In some embodiments, suitable pharmaceutical carriers or vehicles include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In some embodiments, the pharmaceutical composition can also contain minor amounts of wetting or emulsifying agents, or pH buffering agents. In addition, auxiliary, stabilizing, thickening, lubricating and coloring agents can be used.

Pharmaceutical compositions can be manufactured by means of conventional mixing, dissolving, granulating, dragee-making, levigating, emulsifying, encapsulating, entrapping or lyophilizing processes. Pharmaceutical compositions can be formulated in conventional manner using one or more physiologically acceptable carriers, diluents, excipients or auxiliaries, which facilitate processing of compounds disclosed herein into preparations which can be used pharmaceutically. Proper formulation is dependent upon the route of administration chosen.

The present pharmaceutical compositions can take the form of solutions, suspensions, emulsions, tablets, pills, pellets, capsules, capsules containing liquids, powders, sustained-release formulations, suppositories, aerosols, sprays, suspensions, or any other form suitable for use. Other examples of suitable pharmaceutical vehicles have been described in the art (see Remington's Pharmaceutical Sciences, Philadelphia College of Pharmacy and Science, 19th Edition, 1995).

According to another aspect of the invention, it provides methods for using the composition of the present invention. In one embodiment, the composition of the present invention can be used to inhibit, reduce, or minimize one or more adverse effects of the active ingredient, e.g., without the agent. In another embodiment, the composition of the present invention can be used to treat one or more conditions or diseases treatable by the active ingredient, e.g., by administering the composition of the active ingredient and the agent, etc. In yet another embodiment, the composition of the present invention can be used to treat one or more conditions or diseases treatable by the active ingredient with decreased or reduced adverse effect(s) of the active ingredient. In still some embodiments, the active ingredient is an oligonucleotide decoy including one or more binding sites for EGR1 and the composition of the present invention comprising the active ingredient can be used to treat pain or related conditions, In general, "treating" or "treatment" of any condition, disease or disorder refers, in some embodiments, to ameliorating the condition, disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to inhibiting the condition, disease or disorder, either physically, (e.g., stabilization of a discernible symptom), physiologically, (e.g., stabilization of a physical parameter) or both. In some embodiments, "treating" or "treatment" refers to delaying the onset of a condition, disease, or disorder.

The terms "minimizing," "inhibiting," and "reducing," or any variation of these terms, includes any measurable decrease or complete inhibition or reduction to achieve a desired result. For example, there may be a decrease of 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of activity compared to normal. "Prevention" or "preventing" refers to (1) a reduction in the risk of acquiring a disease or disorder (e.g., causing at least one of the clinical symptoms of a disease not to develop in a patient that may be exposed to or predisposed to the disease but does not yet experience or display symptoms of the disease), or (2) a reduction in the likely severity of a symptom associated with a disease or disorder (e.g., reducing the likely severity of at least one of the clinical symptoms of a disease in a patient that may be exposed to or predisposed to the disease but does not yet experience or display symptoms of the disease).

In still some embodiments, the active ingredient is an oligonucleotide decoy including one or more binding sites for EGR1 and the composition of the present invention comprising the active ingredient can be used to treat, pre-treat, or prevent pain or related conditions. In general, "pain" refers to an unpleasant sensory and emotional experience that is associated with actual or potential tissue damage or described in such terms. All of the different manifestations and qualities of pain, including mechanical pain (e.g., induced by a mechanical stimulus or by body motion; mechanical hyperalgesia or allodynia), temperature-induced pain (e.g., pain induced by hot, warm or cold temperatures), and chemically-induced pain (e.g., pain induced by a chemical) are included. In certain embodiments, pain is chronic, sub-chronic, acute, or sub-acute. "Chronic" refers to a period of time comprising months (e.g., at least two months) or years. "Sub-acute" refers to a period of time comprising hours (e.g., 1 h-24 h). "Sub-chronic" refers to a period of time comprising days or months (e.g., less than two months). In certain embodiments, pain features hyperalgesia (i.e., an increased sensitivity to a painful stimulus) or allodynia (i.e., a painful response to a usually non-painful stimulus). Pain can be inflammatory pain, neuropathic pain, muscular pain, skeletal pain, post-surgery pain, arthritis pain, or diabetes pain. In certain embodiments, pain is pre-existing in a patient. In other embodiments, pain is iatrogenic, induced in a patient (e.g., post-operative pain).

In some embodiments, pain or pain related conditions include nociceptive signaling. In general "nociceptive signaling" refers to molecular and cellular mechanisms involved in the detection of a noxious stimulus or of a potentially harmful stimulus, which leads to the perception of pain, including neurotransmitter synthesis and release, neurotransmitter-induced signaling, membrane depolarization, and related intra-cellular and inter-cellular signaling events.

In some other embodiments, pain or pain related conditions include post-operative pain, chronic pain, inflammatory pain, neuropathic pain, muscular pain, and skeletal pain. In certain embodiments, compositions can be used for the prevention of one facet of pain while concurrently treating another symptom of pain.

In certain embodiments, the composition of the present invention can be used for treating or preventing pain in a patient by administering the composition of an oligonucleotide decoy and an agent, wherein the oligonucleotide decoy does not bind to the transcription factors AP1, ETS1 and STAT. In other embodiments, the composition of the present invention can be used for treating or preventing pain in a patient by administering the composition of an oligonucleotide decoy and an agent, wherein the oligonucleotide decoy binds to one or more transcription factors selected from the group consisting of AP1, ETS1, GATA and STAT transcription factors, provided that the pain is not lower back pain due to an intervertebral disc disorder.

In certain embodiments, the composition of the present invention can be used for modulating transcription of a gene present in a cell involved in nociceptive signaling or the perception of pain in a patient by administering the composition of an oligonucleotide decoy, e.g., an oligonucleotide decoy comprising one or more EGR1 binding sites and an agent. In certain embodiments, modulation comprises suppressing or repressing gene expression. "Modulation of gene expression level" refers to any change in gene expression level, including an induction or activation (e.g., an increase in gene expression), an inhibition or suppression (e.g., a decrease in gene expression), or a stabilization (e.g., prevention of the up-regulation or down-regulation of a gene that ordinarily occurs in response to a stimulus, such as a pain-inducing stimulus). In other embodiments, modulation comprises stabilizing gene expression. In still other embodiments, modulation comprises activating or inducing gene expression. In certain embodiments, the gene is involved in nociceptive signaling. Genes involved in nociceptive signaling include, but are not limited to, genes encoding membrane proteins (e.g., ion channels, membrane receptors, etc.), soluble signaling molecules (e.g., intracellular signaling molecules or neurotransmitters), synthetic enzymes (e.g., neurotransmitter synthesis enzymes), and transcription factors. Specific examples of such genes include, but are not limited to, BDKRB2, HTR3A, SCN9A, BDNF, GRM5, NOS1, GCH1, CDK5R1, CACNA1B, P2XR3 and PNMT.

In other embodiments, the composition of the present invention can be used for modulating nociceptive signaling in a cell by contacting the cell with the composition of an oligonucleotide decoy, e.g., an oligonucleotide decoy comprising one or more EGR1 binding sites and an agent. In certain embodiments, modulation comprises suppressing or repressing nociceptive signaling. In certain embodiments, modulating nociceptive signaling in a cell comprises modulating, e.g., increasing, proteolysis of a protein involved in nociceptive signaling in said cell. For instance, abnormally high proteasome activity has been linked to strong deficits of neuronal plasticity (i.e., a major cellular feature of pain). In certain embodiments, modulation comprises activation of an inhibitor of nociceptive signaling.

In still other embodiments, the composition of the present invention can be used for modulating a protein involved in nociceptive signaling in a cell by contacting the cell with the composition of an oligonucleotide decoy, e.g., an oligonucleotide decoy comprising one or more EGR1 binding sites and an agent. In certain embodiments, modulation of protein degradation comprises stimulating proteosome function. In certain embodiments, the protein is involved in nociceptive signaling. Proteins involved in nociceptive signaling include, but are not limited to membrane proteins (e.g., ion channels, membrane receptors, etc.), soluble signaling molecules (e.g., intracellular signaling molecules or neurotransmitters), synthetic enzymes (e.g., neurotransmitter synthesis enzymes), and transcription factors. Specific examples of such proteins include, but are not limited to, BDKRB2, HTR3A, SCN9A, BDNF, GRM5, NOS1, GCH1, As used herein, the term "effective" (e.g., "an effective amount") means adequate to accomplish a desired, expected, or intended result. An effective amount can be a therapeutically effective amount. A "therapeutically effective amount" refers to the amount of an active ingredient that, when administered to a subject, is sufficient to effect such treatment of a particular disease or condition. The "therapeutically effective amount" will vary depending on the active ingredient, the disease or condition, the severity of the disease or condition, and the age, weight, etc., of the subject to be treated.

In certain embodiments, one or more active ingredients, such as oligonucleotide decoys, optionally in a composition (e.g., a pharmaceutical composition) comprising an in vivo stabilizing amount of an agent, are provided in a kit. In certain embodiments, the kit includes an instruction, e.g., for using said one or more active ingredients or the composition comprising the active ingredients. In certain embodiments, said instruction describes one or more of the methods of the present invention, e.g., a method for preventing or treating pain, a method of modulating gene expression in a cell, a method for modulating nociceptive signaling in a cell, a method for modulating protein degradation in a cell, etc. In certain embodiments, the active ingredients optionally in a composition (e.g., a pharmaceutical composition) are provided in a kit are provided in lyophilized form. In certain related embodiments, a kit that comprises one or more lyophilized components further comprises a solution (e.g., a pharmaceutically acceptable saline solution) that can be used to resuspend said one or more of the active ingredients and optional agent.

In general, compositions of the present invention can be administered by any convenient route, for example, by infusion or bolus injection, by absorption through epithelial or mucocutaneous linings (e.g., oral mucosa, rectal and intestinal mucosa, etc.), or orally. Administration can be systemic or local. Various delivery systems are known, including, e.g., encapsulation in liposomes, microparticles, microcapsules, capsules, etc., that can be used for administration purposes. Methods of administration include, but are not limited to, intradermal, intramuscular, intraperitoneal, intravenous, subcutaneous, intranasal, epidural/peridural, oral, sublingual, intranasal, intracerebral, intravaginal, transdermal, rectally, by inhalation or topically, particularly to the ears, nose, eyes, or skin. In certain embodiments, more than one active ingredient is administered to a patient in a composition comprising an agent, and optionally more than one agent. The preferred mode of administration is left to the discretion of the practitioner, and will depend in-part upon the site of the medical condition.

In specific embodiments, it may be desirable to administer one or more compositions locally to the area in need of treatment. This can be achieved, for example, and not by way of limitation, by local infusion during surgery, topical application (e.g., in conjunction with a wound dressing after surgery), by injection, by means of a catheter, by means of a suppository, or by means of an implant, said implant being of a porous, non-porous, or gelatinous material, including membranes, such as sialastic membranes, or fibers. In some embodiments, administration can be by direct injection at the site (e.g., former, current, or expected site) of pain.

In certain embodiments, it may be desirable to introduce one or more compositions into the nervous system by any suitable route, including but not restricted to intraventricular, intrathecal, perineural or epidural/peridural injection. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant.

A dose can be administered and then repeated as needed as determined by those of ordinary skill in the art. Thus, in some embodiments, a single dose is contemplated. In other embodiments, two or more doses are contemplated. Where more than one dose is administered to a subject, the time interval between doses can be any time interval as determined by those of ordinary skill in the art. For example, the time interval between doses can be about 1 hour to about 2 hours, about 2 hours to about 6 hours, about 6 hours to about 10 hours, about 10 hours to about 24 hours, about 1 day to about 2 days, about 1 week to about 2 weeks, or longer, or any time interval derivable within any of these recited ranges. Dosage forms can, for example, be adapted to be administered to a patient no more than a certain number per day, such as no more than twice per day, or only once per day. Dosing can be provided alone or in combination with other drugs and can continue as long as required for effective treatment or prevention, such as effective treatment or prevention of pain.

Combination Therapy

In certain embodiments, compositions of the present invention can be used in combination therapy with at least one other therapeutic agent. The other therapeutic can be another composition comprising an active ingredient. The active ingredient/agent composition and the therapeutic agent can act additively or synergistically. In some embodiments, administration of both the active ingredient/agent composition and the therapeutic agent is concurrent. In other embodiments, an active ingredient/agent composition is administered prior or subsequent to administration of another therapeutic agent.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

The use of the term "or" in the claims is used to mean "and/or" unless explicitly indicated to refer to alternatives only or the alternatives are mutually exclusive. It is specifically contemplated that any listing of items using the term "or" means that any of those listed items may also be specifically excluded from the related embodiment.

Throughout this application, the term "about" is used to indicate that a value includes the standard deviation of error for the device or method being employed to determine the value.

EXAMPLES

Example 1

Clinical Response Score of Oligonucleotide Formulations

A method was developed to identify the appropriate amount of calcium to add to a formulation in order to prevent clinical signs and adverse events following the intrathecal delivery of an oligonucleotide.

Briefly, rats were anesthetized using isoflurane, injected intrathecally (percutaneous delivery, L5/6, 0.02 mL), placed in a cage to recover and their behavior was recorded for ~60 min. Using a saline+oligonucleotide formulation (double stranded, 23 base pairs, molecular weight=14092.92 g/mol, % GC=69.5%, sense strand: 5'-GTATGCGTGGGCG-GTGGGCGTAG-3'), thirteen spontaneous or evoked clinical signs that can occur following the delivery of an oligonucleotide were identified: tail shaking, tail stiffness, tail wagging, hunched back, vocalization, agitation, freezing behavior, distress/seizure, rear/hindpaw motor dysfunction, exaggerated vocalization following tail pinch, exaggerated escape following tail pinch, induced wagging/stiffness following tail pinch. The presence or absence of a sign during the observation period was numerically recorded by 1 or 0, respectively. The performance of a formulation to prevent the occurrence of those signs was judged based on its total numerical score out of 13 and was compared to the score of a control, saline intrathecal injection.

Figure 1:
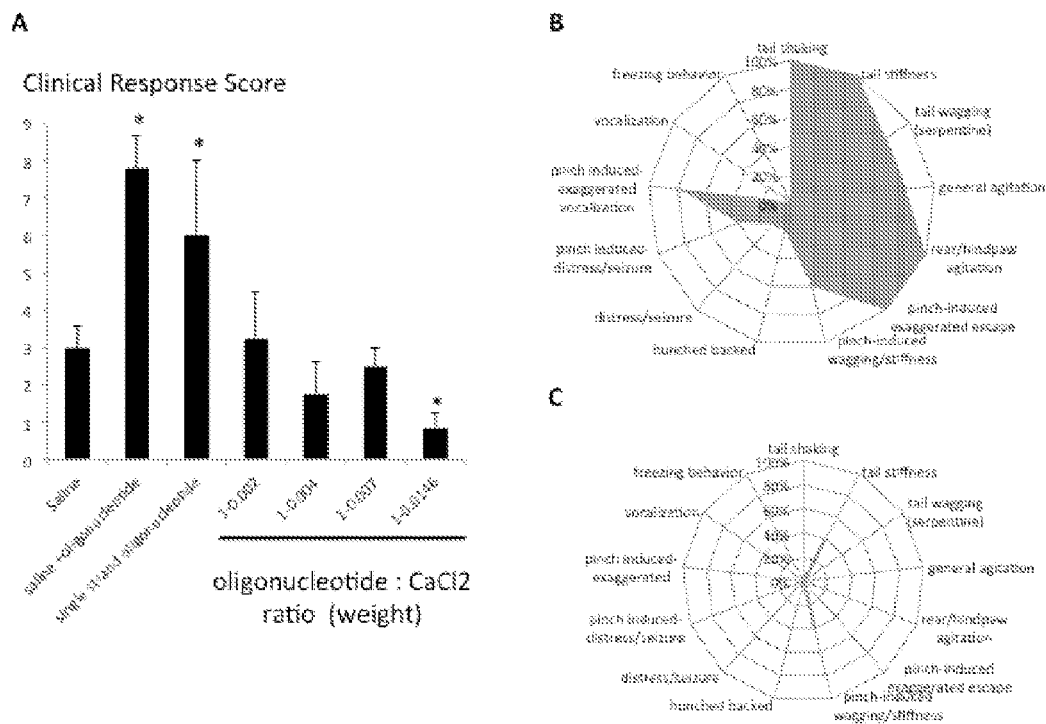
FIG. 1: clinical response scores of oligonucleotide formulations.

A screening method was developed in rats to determine the appropriate molar ratio of $CaCl_2$ (dihydrate $CaCl_2.2H_2O$, molecular weight=147.02 g/mol) relative to the oligonucleotide that eliminated these effects. Briefly, rats were lightly anesthetized in order to perform a percutaneous lumbar IT injection of the oligonucleotide formulation (100 mg/mL, 0.02 mL). After the injection, animals were allowed to recover from anesthesia and placed in a cage. Clinical signs were observed for approximately 1 h and a clinical score based on the occurrence of predetermined clinical signs was calculated. In an iterative manner, several formulations of the oligonucleotide that contained weight ratios of oligonucleotide: $CaCl_2$ ranging from 1:0.002 gram (molar ratio of 1:0.2) to 1:0.026 gram (molar ratio of 1:2.64) were tested. Results indicated that clinical signs were eliminated starting at a weight ratio of oligonucleotide:$CaCl_2$ of 1:0.0146 gram (molar ratio of 1:1.4 M). The effect was maintained up to the highest tested ratio. Based on these results, a fixed weight ratio of oligonucleotide:$CaCl_2$ of 1:0.0198±0.003 (molar ratio of 1:1.8±0.3 M) was determined to be optimal for preventing clinical signs that can occur upon the administration of an oligonucleotide into the CSF (FIG. 1). Further experiments showed that injecting a single strand oligonucleotide produced the same clinical reactions compared to a double-stranded one, confirming a class-effect for nucleotide-based compounds (FIG. 1).

Example 2

Characterizing an Oligonucleotide:Calcium Binding Relationship

Figure 2:
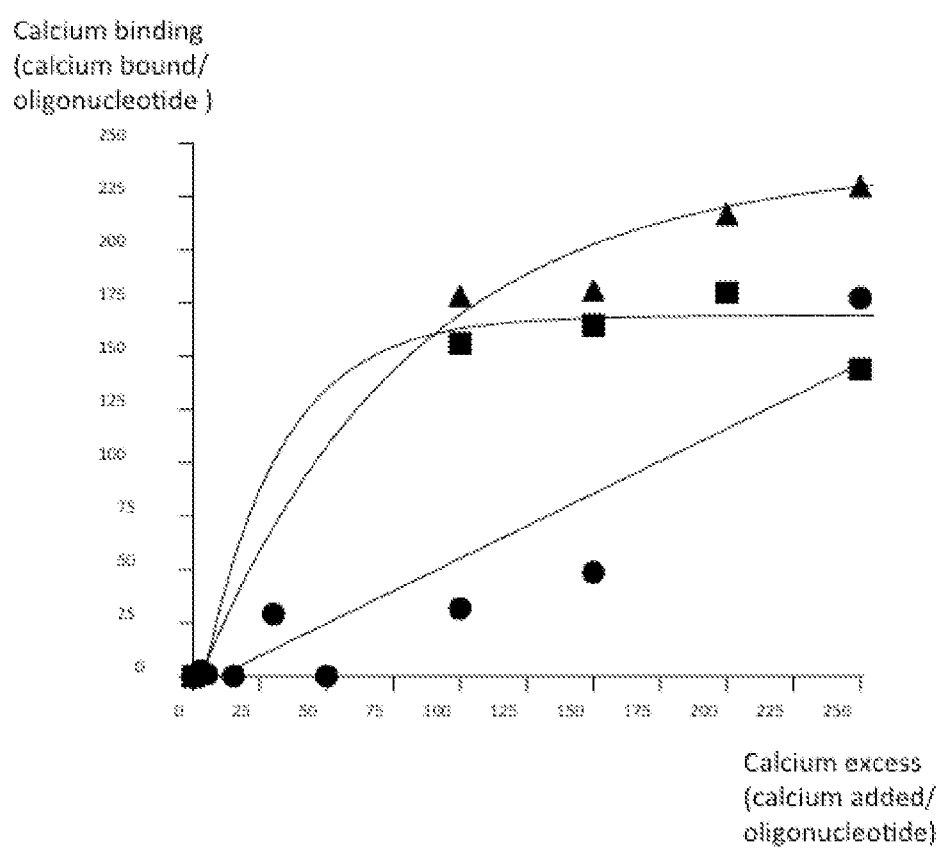
FIG. 2: analysis of an oligonucleotide-calcium binding relationship. Oligonucleotide (0.05 mM to 3 mM) was incubated in presence of various concentrations of $CaCl_2$ (0.14 to 25 mM). Following incubation of $CaCl_2$ and oligonucleotide, the amount of free calcium remaining in the solution was measured using o-cresolphthalein, a dye binding to free calcium (Calcium Colorimetric Assay Kit, BioVision). The quantity of calcium bound to the oligonucleotide was calculated as the difference between the calcium initially introduced in the solution minus the free calcium remaining after incubation (30-60 min). The ratio of concentrations of calcium added in the solution divided by the oligonucleotide concentration was plotted against the concentration of calcium bound to the oligonucleotide divided by the oligonucleotide concentration (circles). The relationship was linear: $R^2=0.89$, slope=0.61, showing that the majority of the calcium was bound to the oligonucleotide. The same experiments were performed in presence of a higher ionic strength by adding NaCl in 2 (triangles) or 12 (squares) fold excess of the calcium concentration. N=1-4 per condition, mean data are presented, oligonucleotide molecular weight=14092.92 g/mol, $CaCl_2$ molecular weight=147.02 g/mol.

Experiments were conducted to characterize a oligonucleotide:calcium binding relationship. Particular efforts were dedicated to characterize the amount of calcium remaining free, unbound to the oligonucleotide of Example 1 since the concentration of calcium that is introduced in the formulation, depending on the oligonucleotide concentration, can exceed the endogenous CSF calcium concentration. A broad range of formulations containing 1.4 to 250 fold excess of calcium relative to the oligonucleotide concentration were prepared and free calcium measured (FIG. 2).

Figure 3:
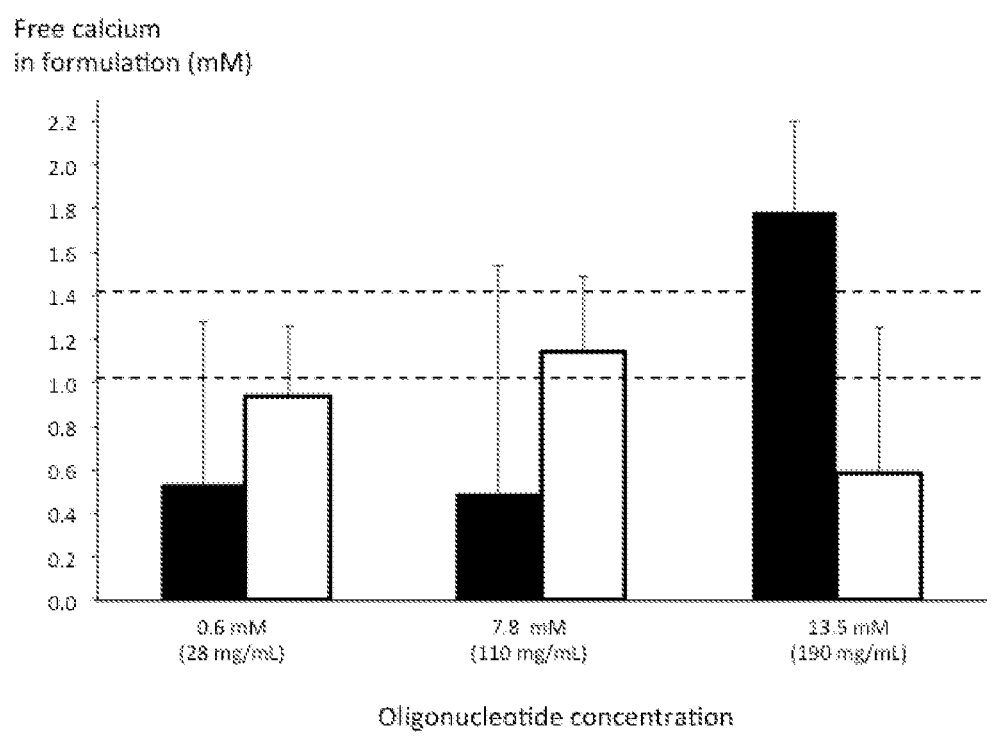
FIG. 3: bar graphs representing free calcium in oligonucleotide formulations. The oligonucleotide was incubated with $CaCl_2$ at a molar ratio of 1.8±0.3 up to the solubility limit of the oligonucleotide (13.5 mM). Three formulations were tested with the following oligonucleotide:$CaCl_2$ concentrations (mM): 0.6:1.08, 7.8:14.04 and 13.5:24.3. After an incubation period of 30 min, free calcium was isolated using ultrafiltration centrifugal membranes (AMICON ULTRA 0.5 ML 3 KDA, Millipore) and its concentration measured using a calcium ion electrode (black bar). A similar experiment was conducted in conditions with ionic strength comparable to cerebrospinal fluid (CSF) (138 mM NaCl, white bar). The dashed bars represent the range of the endogenous level of calcium concentration in the CSF (1-1.4 mM). N=2 per condition, oligonucleotide molecular weight=14092.92 g/mol, CaCl$_2$ molecular weight=147.02 g/mol.

Results showed that the quantity of calcium that binds the oligonucleotide follows a linear relationship ($R^2$=0.89) that increases with the excess of $CaCl_2$. The more calcium is added, the more is bound to the oligonucleotide until a plateau of binding saturation is reached. The binding was also influenced by the overall ionic strength of the tested solution, which was modulated by adding NaCl: the higher the ionic strength, the higher the calcium binding (FIG. 2). Altogether, this set of results indicated that only a small portion of the calcium remains free in presence of the oligonucleotide in the formulation. Due to technical constraints linked to calcium detection assay, initial experiments were conducted with low concentrations of oligonucleotides (0.1-3 mM). Complementary techniques allowing the testing of experimental conditions with higher oligonucleotide concentrations confirmed that up to the oligonucleotide solubility limit (13.5 mM), the amount of calcium that remained free was minimal relative to the concentration initially introduced in the formulation and within range of the endogenous CSF concentration (FIG. 3).

Collectively, these data show that at the defined oligonucleotide:calcium ratio, the calcium introduced in the formulation adequately saturates the calcium binding sites present on the oligonucleotide to prevent the buffering the CSF calcium. Further, they demonstrate that the formulation does not present potential toxicity in terms of artificially introducing a high calcium concentration in the CSF.

Example 3

Pharmacological Analysis of an Oligonucleotide Formulation

Complementary experiments were conducted to ensure that the presence of calcium in the formulation of Example 1 did not alter the pharmacological properties of the oligonucleotide. The tested oligonucleotide is a transcription factor decoy inhibiting the transcription factor EGR1 and prevents the development of pain following injury. Competition ELISA experiments showed that calcium, even at a high excess of concentration, did not impact the affinity of the oligonucleotide for EGR1 (FIG. 4A) nor its stability (FIG. 4B). Behavioral testing of the oligonucleotide in the incisional model and the spared nerve injury preclinical models of pain showed similar efficacy with formulations in presence or absence of calcium (FIG. 5).

Example 4

Long-term Stability Study of an Oligonucleotide Formulation

Following the determination of the optimal oligonucleotide:calcium ratio regarding the oligonucleotide of Example 1, experiments were conducted to further develop a suitable formulation that would provide adequate long-term stability of an oligonucleotide/calcium containing liquid solution. Initial experiments evaluated the need for a buffering agent by preparing oligonucleotide/calcium solutions in water, as oligonucleotides are known to contain a certain amount of buffering capacity. After adjusting the pH to ~7.5, the pH of the solution was evaluated over a 2 week period. pH was not maintained and pH "drift" was noted in the solution (Table 1). Therefore, further experiments were conducted to select an appropriate buffer that would provide adequate pH control and also be compatible with the proposed route of administration (intrathecal). Sodium phosphate was the initial choice of buffer, however experiments indicated compatibility issues with the compound. Low concentrations of sodium phosphate (<5 mM) did not provide adequate buffering capacity to maintain pH, while higher concentrations (≥5 mM) resulted in visible precipitation, presumably due to the formation of calcium phosphate (Table 2). Therefore Tromethamine (Tris), which does not contain phosphates, was evaluated for compatibility and buffering capacity. Experiments indicated that 10 mM Tromethamine (Tris) provided adequate pH control (stable at pH 7.5) and no compatibility issues were observed with the oligonucleotide:calcium containing solution (Table 3).

TABLE 1

Stability of the oligonucleotide:calcium formulation absence of buffer

| Time Interval | Oligonucleotide Concentration, mg/mL | | pH | |
|---|---|---|---|---|
| | Refrigerator (5° C.) | Freezer (−20° C.) | Refrigerator (5° C.) | Freezer (−20° C.) |
| Day 0 | | | 7.47 | |
| | | | 7.5 | |
| Day 3 | 47.7 | 46.8 | 8.28 | 7.58 |
| | 190 | 186.8 | 8.02 | 7.61 |
| Day 7 | 44 | 46.3 | 7.9 | 7.67 |
| | 192 | 187.6 | 7.85 | 7.61 |
| Day 10 | 47.1 | 46.7 | | |
| | 193.8 | 193.8 | | |

Oligonucleotide was formulated with calcium chloride in $H_2O$ at a 1:0.0155 weight ratio (1:1.55 molar ratio) and the pH was adjusted to 7.5 with small amount of diluted sodium hydroxide and diluted hydrochloric acid. The study was performed with ~190 mg/mL and ~50 mg/mL oligonucleotide concentrations at two different storage temperatures of 5° C. and −20° C. The concentration of total oligonucleotide and pH of the AYX1 formulation were monitored for a period of 10 days.

TABLE 2

Stability of the oligonucleotide:calcium formulation with sodium phosphate buffer

| Oligonucleotide Formulation | Day 0 Results | | Day 3 Results | | Day 7 Results | | Day 14 Results | |
|---|---|---|---|---|---|---|---|---|
| | Visual | pH | Visual | pH | Visual | pH | Visual | pH |
| 1:0.001 $CaCl_2$, no sodium phosphate buffer, 4.5 mg/mL of NaCl, Total volume: 1.325 mL[2] | Clear, Colorless | 7.555 | Clear, Colorless | 7.434 | Clear, Colorless | 7.41 | Clear, Colorless | 7.328 |
| 1:0.001 $CaCl_2$, 2.5 mM sodium phosphate buffer, 4.5 mg/mL of NaCl, Total volume: 1.25 mL | Clear, Colorless | 7.491 | Clear, Colorless | 7.47 | Clear, Colorless | 7.457 | Clear, Colorless | 7.415 |
| 1:0.001 $CaCl_2$, 5.0 mM sodium phosphate buffer, 4.5 mg/mL of NaCl, Total volume: 1.25 mL | Clear, Colorless | 7.466 | Clear, Colorless | 7.466 | Clear, Colorless | 7.454 | Clear, Colorless | 7.393 |
| 1:0.002 $CaCl_2$, no sodium phosphate buffer, 4.5 mg/mL of NaCl, Total volume: 1.25 mL | Clear, Colorless | 7.498 | Clear, Colorless | 7.317 | Clear, Colorless | 7.281 | Clear, Colorless | 7.209 |
| 1:0.002 $CaCl_2$, 2.5 mM sodium phosphate buffer, 4.5 mg/mL of NaCl, Total volume: 1.25 mL | Clear, Colorless | 7.546 | Clear, Colorless | 7.521 | Clear, Colorless | 7.478 | Clear, Colorless | 7.421 |

TABLE 2-continued

Stability of the oligonucleotide:calcium formulation with sodium phosphate buffer

| Oligonucleotide Formulation | Day 0 Results Visual | pH | Day 3 Results Visual | pH | Day 7 Results Visual | pH | Day 14 Results Visual | pH |
|---|---|---|---|---|---|---|---|---|
| 1:0.002 CaCl$_2$, 5.0 mM sodium phosphate buffer, 4.5 mg/mL of NaCl, Total volume: 1.25 mL | Clear, Colorless | 7.508 | Slightly turbid | 6.743 | Slightly turbid | 6.724 | Slightly turbid | 6.654 |

Oligonucleotide (112 mg/mL, 7.95 mM) was formulated with calcium chloride in H$_2$O at a 1:0.01 or 1:0.02 weight ratio (1:1-1:2 molar ratio) and the pH was adjusted to 7.5 with small amount of diluted sodium hydroxide and diluted hydrochloric acid. Sodium phosphate was added for buffering of the formulations and sodium chloride was added as the excipient to adjust the osmolality of the formulation. Testing was conducted at the 5° C. storage temperature. The stability and pH of the formulations were monitored for a period of 14 days. Turbidity indicates precipitation occurring within the solution.

TABLE 3

Stability of the oligonucleotide:calcium formulation with Tris buffer

A. Fifteen days stability

| Time Interval | Sample Description | Visual Inspection | pH | Ion Exchange HPLC Purity (Area %) | Size Exclusion HPLC Purity (Area %) |
|---|---|---|---|---|---|
| Day 0 | Drug Product | Clear, colorless | 7.451 | 93.39 | 99.3 |
| | Placebo | Clear, colorless | 7.4 | NA | NA |
| Day 3 | Drug Product | Clear, colorless | 7.522 | NA | NA |
| | Placebo | Clear, colorless | 7.439 | NA | NA |
| Day 7 | Drug Product | Clear, colorless | 7.331 | NA | NA |
| | Placebo | Clear, colorless | 7.546 | NA | NA |
| Day 14 | Drug Product | Clear, colorless | 7.484 | 93.53 | 99.2 |
| | Placebo | Clear, colorless | 7.367 | NA | NA |

B. Three months stability

| Test Method | T = 0 | T = 1 month | T = 2 month | T = 3 month |
|---|---|---|---|---|
| Visual - Color | Colorless | Colorless | Colorless | Colorless |
| Visual - Clarity | Clear | Clear | Clear | Clear |
| Visual - Appearance | Free from visible particulates | Free from visible particulates | Free from visible particulates | Free from visible particulates |
| Total Oligonucleotide Content | 111.8 mg/mL | 111.9 mg/mL | 111.4 mg/mL | 108.4 mg/mL |
| Purity by SEC-HPLC | | | | |
| a. Oligonucleotide Main Peak | 99.30% | 99.20% | 99.20% | 99.20% |
| b. Single Strand Impurities | RRT    % area | RRT    % area | RRT    % area | RRT    % area |
| c. Unspecified Impurities | 0.88    0.61%<br>1.13    0.12% | 0.88    0.59%<br>1.13    0.20% | 0.88<br>0.63%<br>1.14<br>0.21% | 0.88<br>0.63%<br>1.13<br>0.13% |
| Purity by IEX-HPLC | | | | |
| a. Oligonucleotide Main Peaks | 93.6% Total<br>59.6% AWL<br>44.0% AWM | 93.7% Total<br>49.9% AWL<br>43.8% AWM | 92.9% Total<br>49.3% AWL<br>43.6% AWM | 91.3% Total<br>48.8% AWL<br>42.5% AWM |

TABLE 3-continued

| Stability of the oligonucleotide:calcium formulation with Tris buffer | | | | |
|---|---|---|---|---|
| b. impurities | % Area | % Area | % Area | % Area |
| | 2.32% | 2.74% | 2.50% | 3.12% |
| | 0.68% | 1.14% | 0.91% | 0.70% |
| | % Area | % Area | % Area | % Area |
| | 0.30% | 0.27% | 0.31% | 0.31% |
| | 1.79% | 1.53% | 1.79% | 2.88% |
| | 0.73% | 0.27% | 0.61% | 0.98% |
| pH | 7.5 | 7.5 | 7.5 | 7.6 |

Stability of the oligonucleotide:calcium formulation buffered with Tris. Table 3A: Oligonucleotide (112 mg/mL, 7.95 mM) was formulated with calcium chloride in H$_2$O at a 1:0.02 weight ratio (1:2 molar ratio) and the pH was adjusted to 7.5 with small amount of diluted sodium hydroxide and diluted hydrochloric acid. Tris (10 mM final concentration) was added for buffering of the formulation and sodium chloride was added as the excipient to adjust the osmolality of the formulation. Testing was conducted at the 5° C. storage temperature. The stability and pH of the formulations were monitored for a period of 14 days. Additional measures of oligonucleotide stability and integrity (Ion Exchange HPLC purity and Size Exclusion HPLC) were performed at time zero and at 14 days. Table 3B: long term stability of the oligonucleotide: calcium formulation. Oligonucleotide (110 mg/mL, 7.8 mM) was formulated with calcium chloride in H$_2$O at a 1:0.018 weight ratio (1:1.8 molar ratio), the pH was adjusted to 7.5 and Tris added (10 mM final concentration). pH, precipitation (visual observation) and oligonucleotide integrity (size exclusion SEC-HPLC, Ion exchange IEX-HPLC) were measured for 3 months. Three storage conditions were tested: 5° C., 25° C. and 40° C., with similar results. The outcome of the 5° C. storage condition is shown.

It will be apparent to those skilled in the art that many modifications, both to materials and methods, may be practiced without departing from the scope of this disclosure. Accordingly, the present embodiments are to be considered as illustrative and not restrictive, and the invention is not to be limited to the details given herein, but may be modified within the scope and equivalents of the appended claims.

All publications and patents cited herein are incorporated by reference in their entirety.

The invention claimed is:

1. A pharmaceutical composition formulated for administration to cerebrospinal fluid and useful for the treatment of pain or modulation of nociceptive signaling, comprising:
   a) an oligonucleotide decoy having one or more EGR1 transcription factor binding sites; and
   b) an in vivo stabilizing amount of a calcium ion,
   wherein the oligonucleotide decoy is associated with neuromuscular adverse effects in vivo caused by the administration of the oligonucleotide decoy to cerebrospinal fluid without the calcium ion, said adverse effects resulting from the oligonucleotide decoy substantially binding endogenous calcium ion present in the cerebrospinal fluid, and
   wherein the in vivo stabilizing amount is the amount that substantially saturates the binding sites of the oligonucleotide decoy to the calcium ion thereby preventing the oligonucleotide decoy from substantially binding endogenous calcium ion present in the cerebrospinal fluid.

2. The pharmaceutical composition of claim 1, wherein the oligonucleotide decoy comprises SEQ ID NOs: 3, 40, 41, 42, or 45.

3. The pharmaceutical composition of claim 1, formulated for administration by injection.

4. The pharmaceutical composition of claim 1, formulated for intrathecal administration.

5. The pharmaceutical composition of claim 1, wherein the molar ratio or the weight ratio of the oligonucleotide decoy to the calcium ion ranges from about 1:1000 to about 1000:1.

6. The pharmaceutical composition of claim 1, wherein the calcium ion is comprised in calcium chloride, and wherein the weight ratio of the oligonucleotide decoy to calcium chloride is from about 1:1, 2:1, 4:1, 5:1, 15:1, 30:1, 50:1, 100:1, 200:1, 250:1, 300:1, 400:1, or 500:1, or any range derivable therein.

7. The pharmaceutical composition of claim 1 further comprising a buffer.

8. The pharmaceutical composition of claim 1, formulated for administration by infusion.

9. The pharmaceutical composition of claim 1, formulated for intraventricular administration.

10. The pharmaceutical composition of claim 1, formulated for epidural administration.

11. A pharmaceutical composition formulated for administration to cerebrospinal fluid and useful for the treatment of pain or modulation of nociceptive signaling, comprising:
   a) an oligonucleotide decoy comprising SEQ ID NO:42; and
   b) an in vivo stabilizing amount of a calcium ion,
   wherein the oligonucleotide decoy is associated with neuromuscular adverse effects in vivo caused by the administration of the oligonucleotide decoy to cerebrospinal fluid without the calcium ion, said adverse effects resulting from the oligonucleotide decoy substantially binding endogenous calcium ion present in the cerebrospinal fluid, and wherein the in vivo stabilizing amount is the amount that substantially saturates the binding sites of the oligonucleotide decoy to the calcium ion thereby preventing the oligonucleotide decoy from substantially binding endogenous calcium ion present in the cerebrospinal fluid.

12. The pharmaceutical composition of claim 11, formulated for administration by injection.

13. The pharmaceutical composition of claim 11, formulated for intrathecal administration.

14. The pharmaceutical composition of claim 11, wherein the molar ratio, or the weight ratio, of the oligonucleotide decoy to the calcium ion ranges from about 1:1000 to about 1000:1.

15. The pharmaceutical composition of claim 11, wherein the calcium ion is comprised in calcium chloride, and wherein the weight ratio of the oligonucleotide decoy to calcium chloride is from about 1:1, 2:1, 4:1, 5:1, 15:1, 30:1, 50:1, 100:1, 200:1, 250:1, 300:1, 400:1, or 500:1, or any range derivable therein.

16. The pharmaceutical composition of claim 11, further comprising a buffer.

17. The pharmaceutical composition of claim 11, formulated for administration by infusion.

18. The pharmaceutical composition of claim 11, formulated for intraventricular administration.

19. The pharmaceutical composition of claim 11, formulated for epidural administration.

20. A pharmaceutical composition formulated for administration to cerebrospinal fluid and useful for the treatment of pain or modulation of nociceptive signaling, comprising:
   a) an oligonucleotide decoy comprising SEQ ID NO:42; and
   b) $CaCl_2$,
   wherein the oligonucleotide decoy and $CaCl_2$ are present in the composition in a molar ratio of 1:0.2 M to 1:2.64 M.

21. The pharmaceutical composition of claim 20, wherein the oligonucleotide decoy and $CaCl_2$ are present in the composition in a molar ratio of 1:1.4 M.

22. The pharmaceutical composition of claim 20, wherein the oligonucleotide decoy and $CaCl_2$ are present in the composition in a molar ratio of 1:1.8±0.3 M.

23. The pharmaceutical composition of claim 20, formulated for administration by injection.

24. The pharmaceutical composition of claim 20, formulated for intrathecal administration.

25. The pharmaceutical composition of claim 20, formulated for administration by infusion.

26. The pharmaceutical composition of claim 20, formulated for intraventricular administration.

27. The pharmaceutical composition of claim 20, formulated for epidural administration.

28. The pharmaceutical composition of claim 20, further comprising a buffer.

* * * * *